(12) United States Patent
Kubo et al.

(10) Patent No.: US 9,040,492 B2
(45) Date of Patent: May 26, 2015

(54) DOUBLE-STRANDED LIPID-MODIFIED RNA HAVING HIGH RNA INTERFERENCE EFFECT

(75) Inventors: Takanori Kubo, Hiroshima (JP); Hideki Ohba, Tosu (JP); Hidekazu Toyobuku, Osaka (JP); Hirotake Hayashi, Osaka (JP)

(73) Assignees: NATIONAL INSTITUTE OF ADVANCED INDUSTRIAL SCIENCE AND TECHNOLOGY, Tokyo (JP); OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 12/935,546

(22) PCT Filed: Mar. 31, 2009

(86) PCT No.: PCT/JP2009/056638
§ 371 (c)(1),
(2), (4) Date: Sep. 29, 2010

(87) PCT Pub. No.: WO2009/123185
PCT Pub. Date: Oct. 8, 2009

(65) Prior Publication Data
US 2011/0034545 A1 Feb. 10, 2011

(30) Foreign Application Priority Data
Mar. 31, 2008 (JP) .................. 2008-094154

(51) Int. Cl.
*A01N 43/04* (2006.01)
*C12N 15/11* (2006.01)

(52) U.S. Cl.
CPC ...... *C12N 15/111* (2013.01); *C12N 2310/3515* (2013.01); *C12N 2320/32* (2013.01)

(58) Field of Classification Search
None
See application file for complete search history.

(56) References Cited

U.S. PATENT DOCUMENTS

| 2004/0192626 | A1  | 9/2004  | McSwiggen et al. |
| 2004/0249178 | A1* | 12/2004 | Vargeese et al. ............. 552/506 |
| 2006/0008910 | A1  | 1/2006  | MacLachlan et al. |
| 2006/0014289 | A1* | 1/2006  | Ahmadian et al. ............ 435/458 |
| 2007/0031844 | A1* | 2/2007  | Khvorova et al. ................ 435/6 |
| 2007/0135372 | A1* | 6/2007  | MacLachlan et al. .......... 514/44 |
| 2007/0173476 | A1* | 7/2007  | Leake et al. ..................... 514/44 |
| 2009/0012021 | A1* | 1/2009  | Sood et al. ....................... 514/44 |
| 2010/0298411 | A1  | 11/2010 | Kubo et al. |

FOREIGN PATENT DOCUMENTS

| JP | 2008-501730 A | 1/2008 |
| JP | 2008/154523 A | 7/2008 |
| JP | 2008/167739 A | 7/2008 |
| WO | WO 03/074654 A2 * | 9/2003 |
| WO | 2004/065601 A2 | 8/2004 |
| WO | 2004/090105 A2 | 10/2004 |
| WO | 2007/030619 A2 | 3/2007 |
| WO | 2007/056861 A1 | 5/2007 |
| WO | 2007/112107 A2 | 10/2007 |

OTHER PUBLICATIONS

Elbashir, Sayda M., et al., "Functional anatomy of SiRNAs for mediating efficient RNAi in *Drosophila melanogaster* embryo lysate", The EMBO Journal, vol. 20, No. 23, pp. 6877-6888, 2001.
Fire, Andrew et al., "Potent and specific genetic interference by double-stranded RNA in *Caenorhabditis elegans*", Nature, vol. 391, pp. 806-811, Feb. 1998.
Kim, Dong-Ho et al., "Synthetic dsRNA Dicer substrates enhance RNAi potency and efficacy", Nature Biotechnology, vol. 23, No. 2, pp. 222-226, Feb. 2005.
Kubo, T., et al., 2007nen Nippon Kagakukai Nishi Nippon Taikai Koen Yosishu, pp. 267, 2G1-17, 2007.
Kubo, Takanori et al., "Chemically modified symmetric and asymmetric duplex RNAs: An enhanced stability to nuclease degradation and gene silencing effect", Biochemical and Biophysical Research Communications, vol. 365, pp. 54-61, 2008.
Kubo, Takanori et al., "Modified 27-nt dsRNAs with Dramatically Enhanced Stability in Serum and Long-Term RNAi Activity", Oligonucleotides, vol. 17, pp. 445-464, 2007.
Lorenz, Christina et al., "Steroid and lipid conjugates of siRNAs to enhance cellular uptake and gene silencing in liver cells", Bioorganic & Medicinal Chemistry Letters, vol. 14, pp. 4975-4977, 2004.
Marques, Joao Trindade et al., "A structural basis for discriminating between self and nonself double-stranded RNAs in mammalian cells", Nature Biotechnology, vol. 24, No. 5, pp. 559-565, May 2006.
Zhelev, Zhivko et al., Idenshi Delivery Kenkyukai Dai 7 Kai Symposium Yoshishu, pp. 49, 2007.
Extended European Search Report issued in corresponding EP Application No. 09729165.2 on Aug. 21, 2012 (in the name of National Institute of Advanced Industrial Science and Technology et al.).
Christian Wolfrum et al., "Mechanisms and optimization of in vivo delivery of lipophilic siRNAs", Nature Biotechnology, 2007, 25(10): 1149-1157.
Daniel De Paula et al., "Hydrophobization and bioconjugation for enhanced siRNA delivery and targeting", RNA, 2007, 13: 431-456.
Office Action issued Jan. 7, 2013, in corresponding Israeli Patent Application No. 208374.

* cited by examiner

Primary Examiner — Jennifer McDonald
(74) Attorney, Agent, or Firm — Sughrue Mion, PLLC

(57) ABSTRACT

An object of the present invention is to provide a novel double-stranded RNA that has high resistance to nuclease and cellular uptake efficiency and that can produce an excellent RNA interference effect. The present invention provides a double-stranded lipid-modified RNA comprising an antisense strand having a nucleotide sequence complementary to a target sequence in a target gene, and a sense strand having a nucleotide sequence complementary to the antisense strand, the double-stranded RNA being capable of suppressing the expression of the target gene, and the sense strand having a double-stranded lipid bound directly or via a linker to at least one of the first to sixth nucleotides from the 5' end.

14 Claims, 13 Drawing Sheets

① Unmodified Double-Stranded RNA
② DPPE-Double-Stranded RNA

SEQUENCE LISTING

<160> NUMBER OF SEQ ID NOS: 12

<210> SEQ ID NO 1
<211> LENGTH: 27
<212> TYPE: RNA
<213> ORGANISM: Artificial Sequence
<220> FEATURE:
<223> OTHER INFORMATION: L27A, Sense strand of 27nt dsRNA

<400> SEQUENCE: 1
cuggccuuuc acuacuccua cgagcac                                              27

<210> SEQ ID NO 2
<211> LENGTH: 27
<212> TYPE: RNA
<213> ORGANISM: Artificial Sequence
<220> FEATURE:
<223> OTHER INFORMATION: L27B, Antisense strand of 27nt dsRNA

<400> SEQUENCE: 2
gugcucguag gaguagugaa aggccag                                              27

<210> SEQ ID NO 3
<211> LENGTH: 21
<212> TYPE: RNA
<213> ORGANISM: Artificial Sequence
<220> FEATURE:
<223> OTHER INFORMATION: L21A, Sense strand of 21nt siRNA

<400> SEQUENCE: 3
ggccuuucac uacuccuacg a                                                    21

<210> SEQ ID NO 4
<211> LENGTH: 21
<212> TYPE: RNA
<213> ORGANISM: Artificial Sequence
<220> FEATURE:
<223> OTHER INFORMATION: L21B, Antisense strand of 21nt siRNA

<400> SEQUENCE: 4
guaggaguag ugaaaggcca g                                                    21

<210> SEQ ID NO 5
<211> LENGTH: 27
<212> TYPE: RNA
<213> ORGANISM: Artificial Sequence
<220> FEATURE:
<223> OTHER INFORMATION: v27A, Sense strand of 27nt dsRNA

<400> SEQUENCE: 5
cuuccuacag cacaacaaau gugaaug                                              27

<210> SEQ ID NO 6
<211> LENGTH: 27
<212> TYPE: RNA
<213> ORGANISM: Artificial Sequence
<220> FEATURE:
<223> OTHER INFORMATION: v27B, Antisense strand of 27nt dsRNA

<400> SEQUENCE: 6
cauucacauu uguugugcug uaggaag                                              27

-continued

```
<210> SEQ ID NO 7
<211> LENGTH: 21
<212> TYPE: RNA
<213> ORGANISM: Artificial Sequence
<220> FEATURE:
<223> OTHER INFORMATION: v21A, Sense strand of 21nt siRNA

<400> SEQUENCE: 7
uccuacagca caacaaaugu g                                              21

<210> SEQ ID NO 8
<211> LENGTH: 21
<212> TYPE: RNA
<213> ORGANISM: Artificial Sequence
<220> FEATURE:
<223> OTHER INFORMATION: v21B, Antisense strand of 21nt siRNA

<400> SEQUENCE: 8
cauuuguugu gcuguaggaa g                                              21

<210> SEQ ID NO 9
<211> LENGTH: 24
<212> TYPE: DNA
<213> ORGANISM: Artificial Sequence
<220> FEATURE:
<223> OTHER INFORMATION: Primer for VEGF

<400> SEQUENCE: 9
ccctgatgag atcgagtaca tctt                                           24

<210> SEQ ID NO 10
<211> LENGTH: 18
<212> TYPE: DNA
<213> ORGANISM: Artificial Sequence
<220> FEATURE:
<223> OTHER INFORMATION: Primer for VEGF

<400> SEQUENCE: 10
accgcctcgg cttgtcac                                                  18

<210> SEQ ID NO 11
<211> LENGTH: 19
<212> TYPE: DNA
<213> ORGANISM: Artificial Sequence
<220> FEATURE:
<223> OTHER INFORMATION: Primer for GAPDH

<400> SEQUENCE: 11
ggaaagctgt ggcgtgatg                                                 19

<210> SEQ ID NO 12
<211> LENGTH: 20
<212> TYPE: DNA
<213> ORGANISM: Artificial Sequence
<220> FEATURE:
<223> OTHER INFORMATION: Primer for GAPDH

<400> SEQUENCE: 12
ctgttgctgt agccgtattc                                                20
```

DOUBLE-STRANDED LIPID-MODIFIED RNA HAVING HIGH RNA INTERFERENCE EFFECT

TECHNICAL FIELD

The present invention relates to a double-stranded lipid-modified RNA that can efficiently inhibit the expression of a target gene. More specifically, the present invention relates to a double-stranded lipid-modified RNA that has high nuclease resistance and high cellular uptake efficiency, and that can produce an excellent RNA interference effect. The present invention further relates to a pharmaceutical composition utilizing the double-stranded lipid-modified RNA, and a method for suppressing the expression of a target gene utilizing the double-stranded lipid-modified RNA.

BACKGROUND ART

The development of medicines that can efficiently treat intractable diseases, such as cancer and AIDS, is one of the most important objects in the life science field. One of the methods that has high potential as a solution is the use of gene medicines that acts only on specific genes. Particularly, an RNA interference (RNAi) method using a 21-base-long, short double-stranded RNA (small interfering RNA: siRNA) has been attracting attention recently. The RNAi method was first reported by Fire et al. in 1998 (see Non-Patent Document 1). According to the method reported by Fire et al., an approximately 100 base pair double-stranded RNA that is homologous to a specific region of a gene whose function is to be inhibited is introduced into a cell and digested into about 20- to about 25 base pair double-stranded RNA fragments by the action of Dicer in the cytoplasm. The RNA fragments are then combined with a plurality of proteins to form an RNA/protein complex (this complex is referred to as an "RISC": RNA-Induced Silencing Complex). This complex binds to a homologous region of mRNA produced from the target gene, thereby potently suppressing the gene expression. However, it is reported that when approximately 30 base pair or longer double-stranded RNA is introduced into mammalian cells, an interferon response that is an antiviral response is induced, thus causing the phenomenon of apoptosis. It was thus considered difficult to apply the RNAi method to mammalian cell systems. In view of this problem, Tuschl et al. chemically synthesized a 21-base-long double-stranded RNA that has dangling ends at both 3' ends of the strands, and reported that direct introduction of the 21-base-long double-stranded RNA into mammalian cells can sequence-specifically and potently suppress gene expression, while avoiding an interferon response (see Non-Patent Document 2). Tuschl et al. further synthesized short double-stranded RNAs in which the double-stranded region is 19 base pairs and has dangling ends of varied lengths at the 3' ends or 5' ends, and investigated their RNA interference effects. The results showed that 21-base-long siRNA having 2-base-long dangling ends at both 3' ends produces a very high RNA interference effect, whereas no other types of short double-stranded RNAs produce a remarkable RNA interference effect. Based on this report, the principal method used today is an RNA interference method using a 21-base-long double-stranded RNA having 2-base-long dangling ends at both 3' ends. The method for inhibiting the expression of a target gene using a 21-base-long, short double-stranded RNA is herein referred to as the "siRNA method", to distinguish it from the RNAi method.

Because the siRNA method uses synthetic RNA, sample preparation is comparatively easy, and handling is also easy. Furthermore, very potent effects can be produced. Therefore, the siRNA method has been attracting much attention not only in the life science field, but also in the biotechnology business sector.

However, there are also problems with this excellent siRNA method that must be solved. As described above, siRNA is composed of RNA molecules that are readily digested by the action of nuclease contained in cells or in a medium. Although the double-stranded RNA region has a relatively high resistance to nuclease compared to single-stranded RNA, 19 base pair double-stranded RNA hardly exhibits an RNA interference effect at conventional levels. As such, it has been reported that although synthetic siRNA exhibits a potent suppressive effect on gene expression for about 2 to about 4 days after introduction into cells containing a target gene sequence, its RNA interference effect is sharply reduced thereafter, and is almost completely lost in about 7 days.

Various chemically modified siRNAs have recently been disclosed with the purpose of achieving a high cellular uptake efficiency and a prolonged, highly active RNA interference effect in synthetic RNA. For example, siRNAs terminally modified with an amino group, a thiol group, or an abasic site have been synthesized to enhance resistance to exonuclease digestion. However, it has been reported that terminal modification of 21-base-long siRNA sharply reduces the RNA interference effect in most cases.

A recent report by J. Rossi et al. revealed that a 27 base pair double-stranded RNA has an RNA interference effect that is about 100 times greater than that of a 21-base-long siRNA (see Non-Patent Document 3). This potent effect is considered to be achieved for the following reason: after a 27 base pair RNA is cleaved with Dicer, which is an RNase III-like enzyme, into a 21-base-long siRNA, the siRNA is recognized as is by the protein complex RISC, so that siRNA effects can be produced with high efficiency.

Since 27-base-long RNA can produce an excellent RNA interference effect as described above, expectations for its future use as a gene medicine have been increasing. However, what technical method is useful for further enhancing the RNA interference effect of the 27-base-long RNA is completely unknown. Furthermore, the technical method for enhancing the RNA interference effect of double-stranded RNAs of base lengths other than 27 bases is also unknown.

Double-stranded RNAs that produce an RNA interference effect are usually structured to have one or more dangling ends at the ends. The RNA interference effects of double-stranded RNAs having no dangling end (i.e., blunt-ended) have also been investigated. However, the results suggested that double-stranded RNAs that are blunt-ended on the 5'-end side of the sense strand has an RNA interference effect that is substantially the same as or lower than that of double-stranded RNAs having a dangling end on the 5'-end side of the sense strand (see Non-Patent Document 4).

Lipids have a high affinity to cell membranes and high permeability through cell membranes, and are known to be useful for delivering drugs into cells. Binding such a lipid to a double-stranded RNA that has an RNA interference effect would be expected to enhance the cellular uptake efficiency and increase the RNA interference effect. However, merely binding a lipid to a double-stranded RNA having an RNA interference effect has been known to sharply reduce the RNA interference effect. In the prior art, a lipid-modified RNA that can produce both an excellent RNA interference effect and a useful effect based on the lipid has yet to be constructed.

Non-Patent Document 1: Fire et al., Nature, 391, 806-811 (1998)
Non-Patent Document 2: Tuschl et al., EMBO Journal, 20, 6877-6888 (2001)
Non-Patent Document 3: J. Rossi et al., Nature Biotech., 23, 222-226 (2005)
Non-Patent Document 4: J. T. Marques et al., Nature Biotech., 24, 559-565 (2006).

DISCLOSURE OF THE INVENTION

Problem to be Solved by the Invention

An object of the present invention is to provide a novel double-stranded RNA that has high nuclease resistance and high cellular uptake efficiency and that can produce an excellent RNA interference effect. Another object of the present invention is to provide a pharmaceutical composition utilizing the novel double-stranded RNA, and a method for suppressing the expression of a target gene utilizing the novel double-stranded RNA.

Means for Solving the Problem

The present inventors conducted extensive research to achieve the above objects, and found that when a double-stranded lipid is bound directly or via a linker to at least one of the first to sixth nucleotides from the 5' end of a sense strand of a double-stranded RNA that comprises the antisense strand having a nucleotide sequence complementary to a target sequence in a target gene, and a sense strand having a nucleotide sequence complementary to the antisense strand, and that can suppress the expression of the target gene, the resulting double-stranded RNA has high nuclease resistance and high the cellular uptake efficiency, and can produce an excellent RNA interference effect. The present invention was accomplished as a result of further research, based on this finding.

More specifically, the present invention provides the following double-stranded lipid-modified RNAs, pharmaceutical compositions, use thereof, and method for suppressing the expression of a target gene.

Item 1. A double-stranded lipid-modified RNA comprising an antisense strand having a nucleotide sequence complementary to a target sequence in a target gene, and a sense strand having a nucleotide sequence complementary to the antisense strand, the double-stranded RNA being capable of suppressing expression of the target gene, and the sense strand having a double-stranded lipid bound directly or via a linker to at least one of the first to sixth nucleotides from the 5' end.

Item 2. The double-stranded lipid-modified RNA according to Item 1, which is blunt-ended on the 5'-end side of the sense strand, and is blunt-ended or has a dangling end on the 3'-end side of the sense strand.

Item 3. The double-stranded lipid-modified RNA according to Item 1, which has dangling ends on both the 5'- and 3'-end sides of the sense strand.

Item 4. The double-stranded lipid-modified RNA according to any one of Items 1 to 3, wherein the sense strand consists of 21 to 27 nucleotides.

Item 5. The double-stranded lipid-modified RNA according to Item 2, which is blunt-ended on both the 5'- and 3'-end sides of the sense strand, each of the sense and antisense strands consisting of 27 nucleotides.

Item 6. The double-stranded lipid-modified RNA according to Item 2, which is blunt-ended on both the 5'- and 3'-end sides of the sense strand, each of the sense and antisense strands consisting of 23 nucleotides.

Item 7. The double-stranded lipid-modified RNA according to Item 2, which is blunt-ended on the 5'-end side of the sense strand, the sense strand consisting of 25 nucleotides, and the antisense strand consisting of 23 nucleotides.

Item 8. The double-stranded lipid-modified RNA according to Item 3, wherein each of the sense and antisense strands consists of 21 nucleotides.

Item 9. The double-stranded lipid-modified RNA according to any one of Items 1 to 8, wherein two hydrophobic groups of the double-stranded lipid are the same or different, and each is a saturated or unsaturated fatty acid residue having 6 to 50 carbon atoms.

Item 10. The double-stranded lipid-modified RNA according to any one of Items 1 to 9, wherein the double-stranded lipid is glycerophospholipid, glyceroglycolipid, diacylglycerol, or ceramide.

Item 11. The double-stranded lipid-modified RNA according to any one of Items 1 to 9, wherein the double-stranded lipid is glycerophospholipid.

Item 12. The double-stranded lipid-modified RNA according to Item 11, wherein the double-stranded lipid is phosphatidylethanolamine.

Item 13. The double-stranded lipid-modified RNA according to item 12, wherein the double-stranded lipid is at least one member selected from the group consisting of dimyristoylphosphatidylethanolamine, dipalmitoylphosphatidylethanolamine, 1-palmitoyl-2-oleyl-phosphatidylethanolamine, and dioleoylphosphatidylethanolamine.

Item 14. The double-stranded lipid-modified RNA according to any one of Items 1 to 13, wherein the lipid is bound to at least one of the first to sixth nucleotides from the 5' end of the sense strand via a linker represented by the formula (L-27)

[Chem. 1]

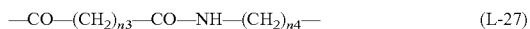

$$-CO-(CH_2)_{n3}-CO-NH-(CH_2)_{n4}- \qquad (L-27)$$

wherein n3 and n4 are the same or different and each represents an integer of 1 to 20.

Item 15. A pharmaceutical composition comprising the double-stranded lipid-modified RNA of any one of Items 1 to 14, and a pharmaceutically acceptable carrier.

Item 16. Use of the double-stranded lipid-modified RNA of any one of Items 1 to 14 to produce a pharmaceutical composition for suppressing the expression of a target gene.

Item 17. A method for suppressing the expression of a target gene, comprising a step of introducing the double-stranded lipid-modified RNA of any one of Items 1 to 14 into a cell.

Effect of the Invention

The double-stranded lipid-modified RNA of the present invention is modified with a double-stranded lipid on the 5'-end side of the sense strand. Based on this structural feature, the double-stranded lipid-modified RNA has a significantly increased RNA interference effect. In particular, because the double-stranded lipid-modified RNA of the present invention has a double-stranded lipid bound to a specific site, a remarkably enhanced nuclease resistance and RNA interference effect are provided without impairing Dicer processing or the RNA's ability to form a complex with RISC, thus greatly contributing to its medicinal applications.

The double-stranded lipid-modified RNA of the invention has a remarkably high ability to be delivered intracellularly, even when used alone. Thus, the double-stranded lipid-modified RNA of the invention can be introduced into a cell without using any known gene transfection reagents, or by using a known gene transfection reagent in a reduced amount. Accordingly, the double-stranded lipid-modified RNA of the invention can suppress the development of cytotoxicity, which is a concern when using conventional gene transfection reagents, thereby ensuring high safety in clinical applications.

Therefore, when using the pharmaceutical composition or the method for suppressing the expression of a target gene that utilizes the double-stranded lipid-modified RNA of the invention, it is clinically possible to more effectively suppress or inhibit the expression of the target gene.

BRIEF DESCRIPTION OF THE DRAWINGS

in FIG. 2A, lane (1) represents 21 nt siRNA, lane (2) represents the RNA of DPPE L21A/L21B, lane (3) represents the RNA of POPE L21A/L21B, lane (4) represents the RNA of DOPE L21A/L21B, and lane (5) represents the RNA of DMPE L21A/L21B; and in FIG. 2B, lane (1) represents 27 nt dsRNA, lane (2) represents the RNA of DPPE L27A/L27B, lane (3) represents the RNA of POPE L27A/L27B, lane (4) represents the RNA of DOPE L27A/L27B, and lane (5) represents the RNA of DMPE L27A/L27B.

in FIG. 7A, lanes (1) and (2) of A-1 represent 21 nt siRNA and the RNA of DPPE v21A/v21B, respectively; and lanes (1), (2), (3), and (4) of A-2 represent 21 nt siRNA, the RNA of POPE v27A/v27B, the RNA of DOPE v27A/v27B, and the RNA of DMPE v27A/v27B, respectively; and in FIG. 7B, the lanes (1), (2), (3), (4), and (5) represent 27 nt dsRNA, the RNA of DPPE v27A/v27B, the RNA of POPE v27A/v27B, the RNA of DOPE v27A/v27B, and the RNA of DMPE v27A/v27B, respectively.

FIG. 11-1 shows the results of the investigation of the cellular uptake efficiencies of the VEGF gene-targeting double-stranded lipid-modified RNAs into HeLa cells;

wherein "FL" denotes images taken with a fluorescence microscope; "Trans" denotes images taken with a phase contrast microscope in the same field of view as that of the FL images; and "Merge" denotes images obtained by superimposing the FL and Trans images.

Figure 2:
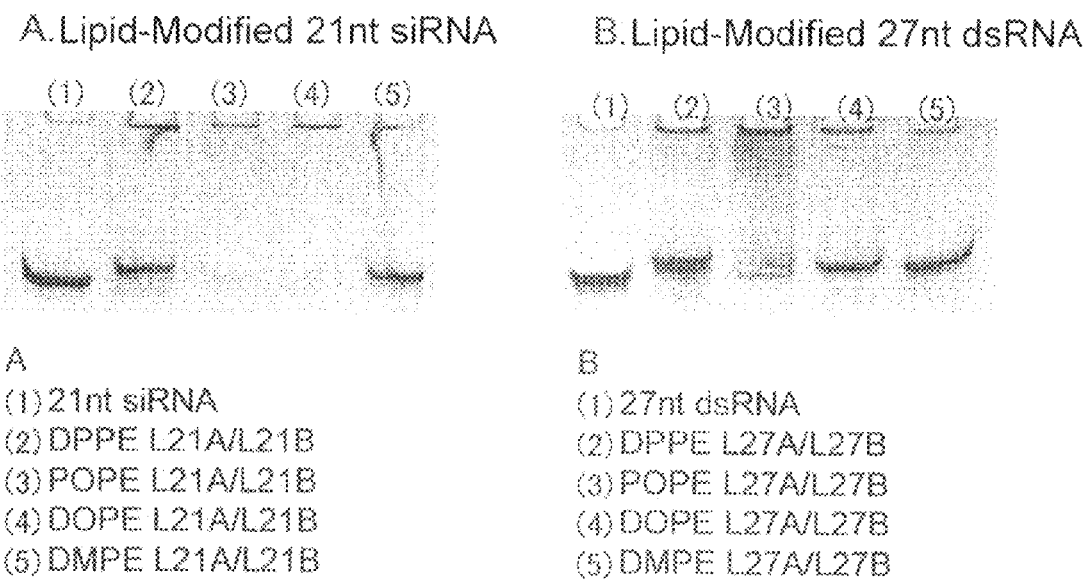
FIG. 2 shows the results of confirming the formation of the double-stranded RNAs of the double-stranded lipid-modified RNAs in Example 1.
Figure 11:
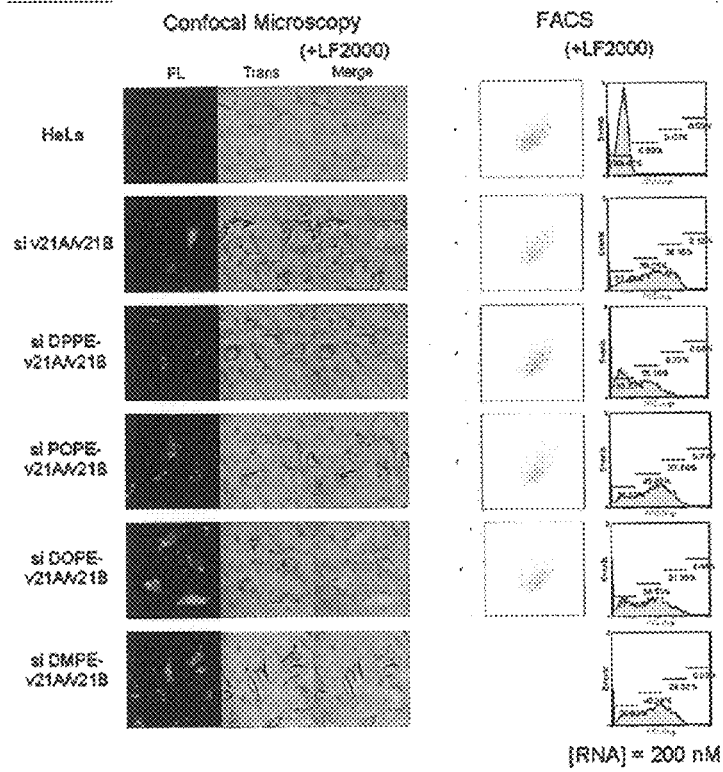
Figure 1:
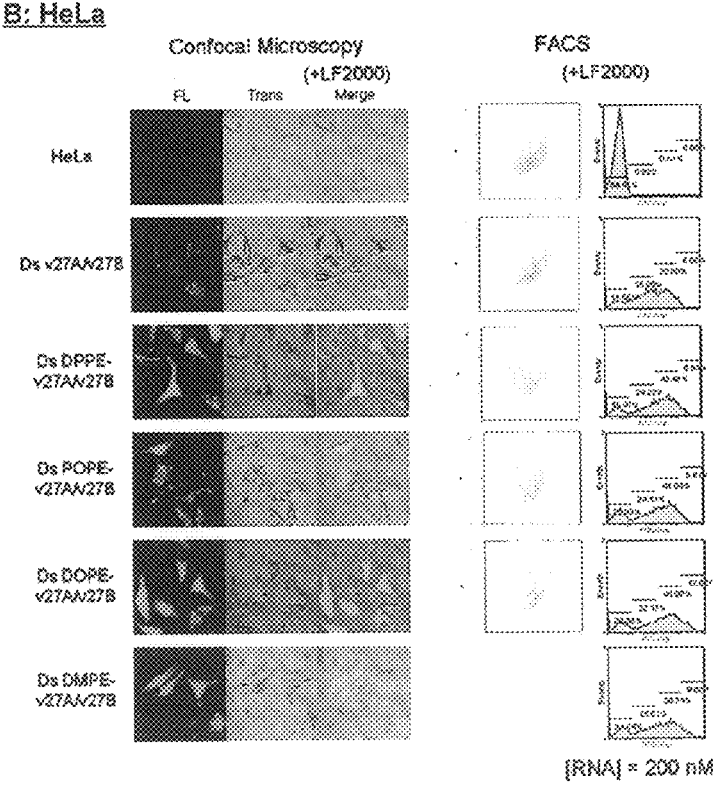
Figure 11:
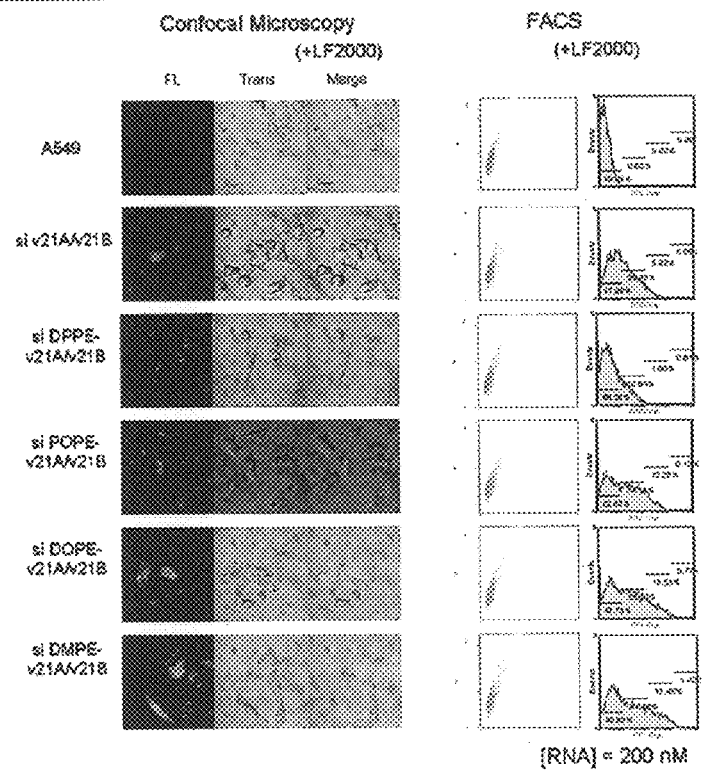
Figure 2:
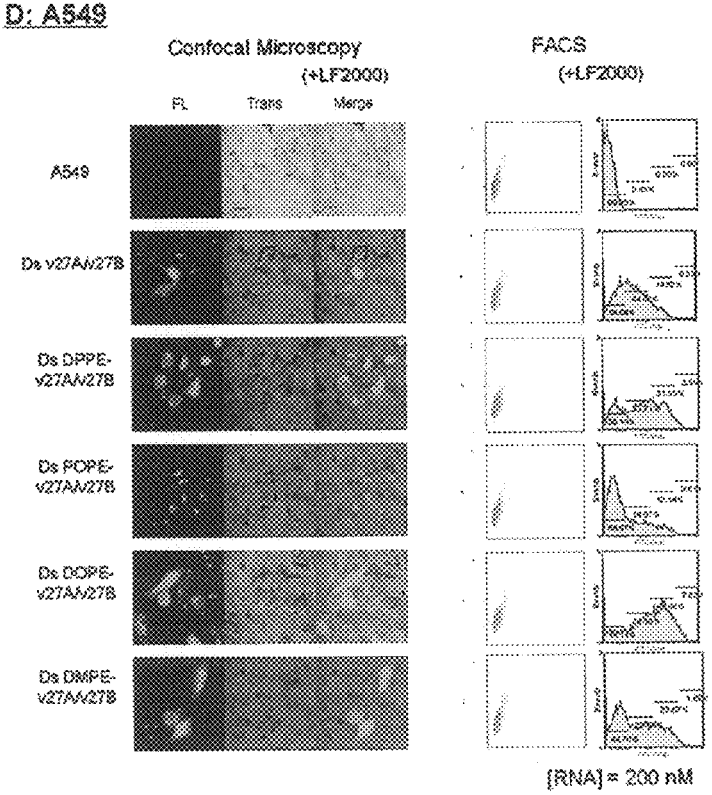

FIG. 11-2 shows the results of the investigation of the cellular uptake efficiencies of the VEGF gene-targeting double-stranded lipid-modified RNAs into A549 cells;

wherein "FL" denotes images taken with a fluorescence microscope; "Trans" denotes images taken with a phase contrast microscope in the same field of view as that of the FL images; and "Merge" denotes images obtained by superimposing the FL and Trans images.

Figure 12:
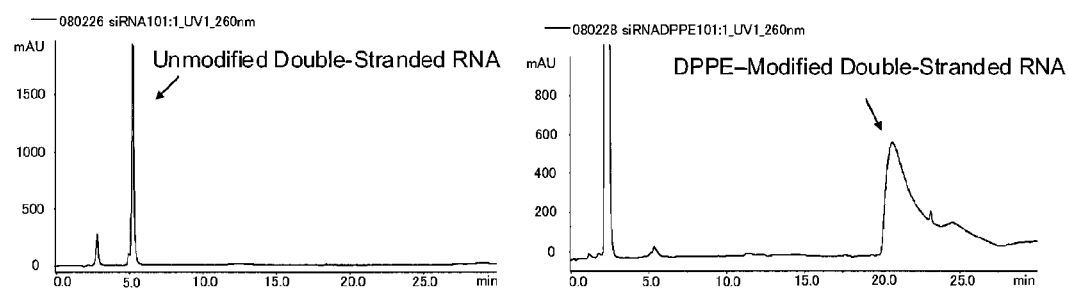

FIG. 12 shows the results of HPLC analysis performed on the double-stranded lipid-modified RNA in Example 3.

Figure 13:
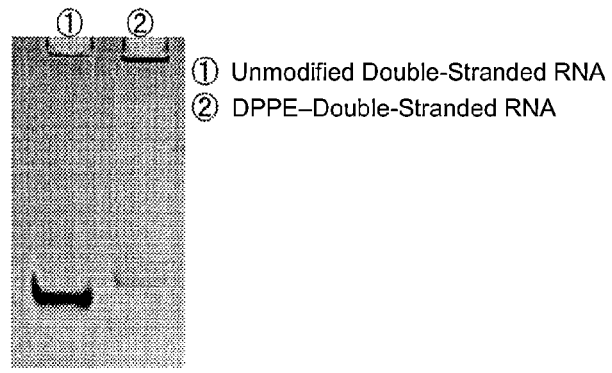

FIG. 13 shows the results of confirming the synthesis of the double-stranded lipid-modified RNA in Example 3.

BEST MODE FOR CARRYING OUT THE INVENTION

In this specification, "blunt end" or "blunt-ended" refers to a terminal structure of double-stranded RNA in which bases in the terminal region of the sense strand and bases in the terminal region of the antisense strand complementary to the sense strand are paired without forming a single-stranded portion (i.e., without forming a projection). The "dangling end" is also called an "overhang". This term refers to a terminal nucleotide sequence structure (a projection) in which a single strand is present without forming a double strand, because complementary bases are not present in the terminal region of a sense strand of a double-stranded RNA or in the terminal region of an antisense strand complementary to the sense strand. In the present specification, the "double-stranded lipid-modified RNA" refers to double-stranded RNA molecules having a double-stranded lipid bound thereto.

The double-stranded lipid-modified RNA of the invention comprises an antisense strand having a nucleotide sequence complementary to a target sequence in a target gene.

Target gene, as used herein, refers to a gene whose expression is suppressed by the RNA interference effect. In the double-stranded lipid-modified RNA of the invention, the target gene is not particularly limited, and can be suitably selected according to the intended use of the double-stranded lipid-modified RNA.

The target sequence of the target gene is not particularly limited insofar as the expression of the gene can be suppressed by the RNA interference effect. The target sequence can be suitably determined according to a known method, for example, by using an NCBI BLAST search, etc. For example, the target sequence may be a region consisting of 19 to 30 bases following the bases "AA" in the exon region that is 50 to 100 bases downstream of the start codon of the coding region (ORF) of the target gene, and having a GC content of about 50%. It is empirically known in this technical field that an excellent RNA interference effect can be produced by using a strand complementary to such a target sequence. The target sequence can also be determined, for example, according to the instructions of IDT (Integrated DNA Technologies, Inc.; Dicer Substrate RNAi Design). Further, a recent report revealed that a double-stranded RNA having a high RNA interference effect can be produced by designing a double-stranded RNA satisfying the following structural features: (i)

having an A/U pair at the 5' end of the antisense strand, (ii) having a G/C pair at the 5' end of the sense strand, and (iii) having about five A/U pairs present in the 5'-end region of the antisense strand; (iv) and the double-stranded RNA not having nine or more G/C pairs (Ui-Tei et al., Nucleic Acids Res., 32, 936-948 (2004)).

When the double-stranded lipid-modified RNA of the invention has no dangling end on the antisense strand, the antisense strand consists of a nucleotide sequence complementary to the target sequence. When a dangling end is present at the 5' end and/or 3' end of the antisense strand, the antisense strand consists of a nucleotide sequence having a nucleotide sequence complementary to the target sequence, and a dangling end nucleotide sequence that is attached to the 5' end and/or the 3' end of the complementary nucleotide sequence.

Insofar as the RNA interference effect can be produced, the number of nucleotides that constitute the antisense strand of the double-stranded lipid-modified RNA of the invention is not particularly limited, and can be suitably selected according to the desired structure of the double-stranded lipid-modified RNA, etc. The number of nucleotides is typically 21 to 27, preferably 21, 23, 25, or 27, and more preferably 21 or 27. When no dangling end is present on the antisense strand, the number of nucleotides that constitute the antisense strand, as used herein, refers to the total number of nucleotides constituting the nucleotide sequence complementary to the target sequence. When a dangling end is present on the sense antisense strand, the number of nucleotides that constitute the antisense strand refers to the sum of the number of nucleotides constituting the dangling end, and the number of nucleotides constituting the nucleotide sequence complementary to the target sequence.

The double-stranded lipid-modified RNA of the invention comprises a sense strand having a nucleotide sequence complementary to the antisense strand.

When the double-stranded lipid-modified RNA of the invention has no dangling end on the sense strand, the sense strand consists of a nucleotide sequence complementary to a part or all of the "nucleotide sequence complementary to a target sequence" of the antisense strand. When a dangling end is present at the 5' end and/or at the 3' end of the sense strand, the sense strand consists of a nucleotide sequence complementary to a part or all of the "nucleotide sequence complementary to a target sequence" of the antisense strand, and a dangling end nucleotide sequence linked to the 5' end and/or the 3' end of the complementary nucleotide sequence of the antisense strand.

Insofar as the RNA interference effect can be produced, the number of nucleotides that constitute the sense strand in the double-stranded lipid-modified RNA of the invention is not particularly limited, and can be suitably selected according to the desired structure of the double-stranded RNA, etc. The number of the nucleotides is typically 21 to 27, preferably 21, 23, 25, or 27, and more preferably 21, 23, or 27. When no dangling end is present on the sense strand, the number of nucleotides that constitute the sense strand, as used herein, refers to the total number of nucleotides constituting the nucleotide sequence complementary to the nucleotide sequence of the target sequence. When a dangling end is present on the sense strand, the number of nucleotides that constitute the sense strand refers to the sum of the number of nucleotides constituting the dangling end, and the number of nucleotides constituting the nucleotide sequence complementary to the nucleotide sequence of the target sequence.

The nucleotides that constitute the sense strand and antisense strand of the double-stranded lipid-modified RNA of the invention are mainly ribonucleotides. To enhance resistance to enzymatic digestion, the RNA sequence may further include various chemically modified nucleotides, such as 2'-O-methyl-modified nucleotides, 2'-F-modified nucleotides, LNA (Locked Nucleic Acid) nucleotides, or deoxyribonucleotides. Particularly, when the double-stranded lipid-modified RNA of the invention has a dangling end, the dangling end of the sense strand and/or the antisense strand may be composed of deoxyribonucleotides. Examples of such chemically modified nucleotides include phosphate backbone-modified nucleotides such as phosphorothioate-modified DNA/RNA and boranophosphate-modified DNA/RNA; 2'-modified nucleotides such as 2'-OMe-modified RNA and 2'-F-modified RNA; modified nucleotides obtained by crosslinking the sugar molecule of a nucleotide, such as LNA (Locked Nucleic Acid) and ENA (2'-O,4'-C-ethylene-bridged nucleic acids); modified nucleotides having different backbones, such as PNA (Peptide Nucleic Acid) and morpholine-nucleotide; base-modified nucleotides such as 5-fluorouridine and 5-propyluridine; and the like.

The structure of the double-stranded lipid-modified RNA of the invention is not particularly limited, insofar as the sense and antisense strands are hybridized into a double strand. For examples, the following structures are preferable: structure (A) in which the double-stranded RNA is blunt-ended (i.e., has a blunt end) on the 5'-end side of the sense strand, and is blunt-ended or has a dangling end (a single-stranded region or a projection) on the 3'-end side of the sense strand; and structure (B) in which the double-stranded RNA has dangling ends on both the 5'- and 3'-end sides of the sense strand. Based on the above structure (A) or (B), the double-stranded lipid-modified RNA can maintain its RNA interference effect, although modified with a double-stranded lipid, and also has remarkably enhanced cellular uptake efficiency. The structure of "having a dangling end on the 3'-end side of the sense strand", as used herein, includes both of the following cases: the case in which the 3'-end region of the sense strand forms a dangling end; and the case in which the 5'-end region of the antisense strand forms a dangling end. The structure of "having a dangling end on the 5'-end side of the sense strand", as used herein, includes both of the following cases: the case in which the 5'-end region of the sense strand forms a dangling end; and the case in which the 3'-end region of the antisense strand forms a dangling end.

To provide a particularly excellent RNA interference effect, for example, the following structures of the double-stranded RNA of the double-stranded lipid-modified RNA of the invention are particularly preferable among the above structures (A) and (B): structure (A-1) in which the double-stranded RNA is blunt-ended on both the 5'- and 3'-end sides of the sense strand, and each of the sense and antisense strands consists of 27 nucleotides; structure (A-2) in which the double-stranded RNA is blunt-ended on both the 5'- and 3'-end sides of the sense strand, and each of the sense and antisense strands consists of 23 nucleotides; structure (A-3) in which the double-stranded RNA is blunt-ended on the 5'-end side of the sense strand, and the sense strand consists of 25 nucleotides, and the antisense strand consists of 23 nucleotides; and structure (B-1) in which the double-stranded RNA has two-nucleotide dangling ends at both 3' ends of the sense and antisense strands, and each of the sense and antisense strands consists of 21 nucleotides.

More specifically, in structures (A-1) and (A-2), the sense and antisense strands are hybridized without forming any dangling ends at the ends. In structure (A-3), the sense and antisense strands are hybridized in such a manner that the double-stranded RNA is blunt-ended on the 5'-end side of the sense strand, and the first and second nucleotides from the 3' end of the sense strand form a dangling end. In structure (B-1), the first to 19th nucleotides from the 5' end of the sense strand and the third to 21st nucleotides from the 3' end of the antisense strand are hybridized in such a manner that the first and second nucleotides from the 3' end of the sense strand form a dangling end, and the first and second nucleotides from 3' end of the antisense strand form a dangling end.

According to the double-stranded lipid-modified RNA of the invention, a lipid is bound to at least one of the first to sixth nucleotides from the 5' end of the sense strand. The double-stranded lipid-modified RNA of the invention has no substitutents bound to any position other than the 5'-end region of the sense strand. More specifically, no portions of the sense strand other than the 5'-end region and the antisense strand have substituents, and these portions only consist of nucleotides. The binding of a lipid only to the 5'-end region of the sense strand enhances cellular uptake efficiency and can also remarkably increase the RNA interference effect. More specifically, in the double-stranded lipid-modified RNA of the present invention, a double-stranded RNA structure, the use of a double-stranded lipid to modify the double-stranded RNA, and the binding site of the double-stranded lipid are structural features that are inseparably related. Based on these structural features, the double-stranded lipid-modified RNA of the invention has excellent cellular uptake efficiency and nuclease resistance, and can produce a remarkably increased RNA interference effect.

In the double-stranded lipid-modified RNA of the invention, the double-stranded lipid bound to the sense strand is not particularly limited, insofar as the lipid has two hydrophobic groups. Examples of the double-stranded lipid include lipids having at least two hydrophobic groups selected from the group consisting of $C_{6-50}$ saturated fatty acid residues and $C_{6-50}$ unsaturated fatty acid residues. Each of the saturated fatty acid residue and the unsaturated fatty acid residue preferably has 8 to 30 carbon atoms, and more preferably 10 to 24 carbon atoms. More specifically, examples of hydrophobic groups of the lipid include fatty acid residues such as capric acid, lauric acid, myristic acid, palmitic acid, stearic acid, arachidic acid, behenic acid, lignoceric acid, myristoleic acid, palmitoleic acid, oleic acid, elaidic acid, vaccenic acid, erucic acid, gadoleic acid, linoleic acid, linolenic acid, and arachidonic acid. To more remarkably produce the effect of the present invention, at least one fatty acid residue selected from myristic acid, palmitic acid, stearic acid, and oleic acid is preferably used as the two hydrophobic groups of the double-stranded lipid in the present invention.

Examples of double-stranded lipids that can be used in the present invention include glycerophospholipid, glyceroglycolipid, diacylglycerol, ceramide, and the like. To further enhance the nuclease resistance, cellular uptake efficiency, and RNA interference effect, glycerophospholipid can be preferably used.

The glycerophospholipid that can be used in the present invention is not particularly limited. Examples of usable glycerophospholipid include phosphatidylethanolamine, phosphatidylglycerol, phosphatidylserine, phosphatidic acid, and phosphatidylinositol, etc.

Examples of phospholipids that can be used in the present invention include phosphatidylethanolamines, such as dilauroylphosphatidylethanolamine, dimyristoylphosphatidylethanolamine, dipalmitoylphosphatidylethanolamine, distearoylphosphatidylethanolamine, dioleoylphosphatidylethanolamine, 1-palmitoyl-2-oleylphosphatidylethanolamine, 1-oleyl-2-palmitoylphosphatidylethanolamine, and dierucoylphosphatidylethanolamine; phosphatidylglycerols, such as dilauroylphosphatidylglycerol, dimyristoylphosphatidylglycerol, dipalmitoylphosphatidylglycerol, distearoylphosphatidylglycerol, dioleoylphosphatidylglycerol, 1-palmitoyl-2-oleyl-phosphatidylglycerol, 1-oleyl-2-palmitoyl-phosphatidylglycerol, and dierucoylphosphatidylglycerol; phosphatidylserines, such as dilauroylphosphatidylserine, dimyristoylphosphatidylserine, dipalmitoylphosphatidylserine, distearoylphosphatidylserine, dioleoylphosphatidylserine, 1-palmitoyl-2-oleyl-phosphatidylserine, 1-oleyl-2-palmitoyl-phosphatidylserine, and dierucoylphosphatidylserine; phosphatidic acids, such as dilauroylphosphatidic acid, dimyristoylphosphatidic acid, dipalmitoylphosphatidic acid, distearoylphosphatidic acid, dioleoylphosphatidic acid, 1-palmitoyl-2-oleylphosphatidic acid, 1-oleyl-2-palmitoyl-phosphatidic acid, and dierucoylphosphatidic acid; and phosphatidylinositols, such as dilauroylphosphatidylinositol, dimyristoylphosphatidylinositol, dipalmitoylphosphatidylinositol, distearoylphosphatidylinositol, dioleoylphosphatidylinositol, 1-palmitoyl-2-oleyl-phosphatidylinositol, 1-oleyl-2-palmitoyl-phosphatidylinositol, and dierucoylphosphatidylinositol. To provide more remarkable nuclease resistance, cellular uptake efficiency, and a more remarkable RNA interference effect, phosphatidylethanolamines may be preferably used. More preferably, dimyristoylphosphatidylethanolamine, dipalmitoylphosphatidylethanolamine, 1-palmitoyl-2-oleylphosphatidylethanolamine, and dioleoylphosphatidylethanolamine can be used.

The manner of binding the double-stranded lipid to the sense strand in the double-stranded lipid-modified RNA of the invention is not particularly limited. The lipid and the sense strand may be bound directly or via a linker (a linkage region). The linker used to bind the lipid to the sense strand does not comprise a nucleic acid.

The linker that can be used is not particularly limited insofar as the lipid and the sense strand are linked therethrough. Examples of usable linkers include those of the following structures:

[Chem. 2]

   (L-1)

—O—CO—O—

   (L-2)

—NH—CO—O—

   (L-3)

—NH—CO—NH—

   (L-4)

—NH—(CH$_2$)$_{n1}$—

   (L-5)

—S—(CH$_2$)$_{n1}$—

   (L-6)

—CO—(CH$_2$)$_{n1}$—CO—

   (L-7)

—CO—(CH$_2$)$_{n1}$—NH—

   (L-8)

—NH—(CH$_2$)$_{n1}$—NH—

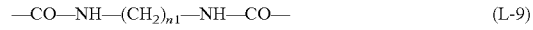   (L-9)

—CO—NH—(CH$_2$)$_{n1}$—NH—CO—

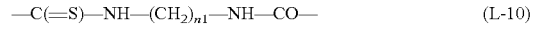   (L-10)

—C(=S)—NH—(CH$_2$)$_{n1}$—NH—CO—

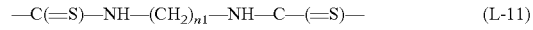   (L-11)

—C(=S)—NH—(CH$_2$)$_{n1}$—NH—C—(=S)—

   (L-12)

—CO—O—(CH$_2$)$_{n1}$—O—CO—

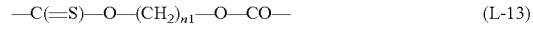   (L-13)

—C(=S)—O—(CH$_2$)$_{n1}$—O—CO—

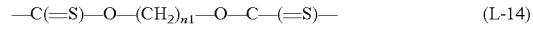   (L-14)

—C(=S)—O—(CH$_2$)$_{n1}$—O—C—(=S)—

$-CO-NH-(CH_2)_{n1}-O-CO-$ (L-15)

$-C(=S)-NH-(CH_2)_{n1}-O-CO-$ (L-16)

$-C(=S)-NH-(CH_2)_{n1}-O-C-(=S)-$ (L-17)

$-CO-NH-(CH_2)_{n1}-O-CO-$ (L-18)

$-C(=S)-NH-(CH_2)_{n1}-CO-$ (L-19)

$-C(=S)-O-(CH_2)_{n1}-NH-CO-$ (L-20)

$-C(=S)-NH-(CH_2)_{n1}-O-C-(=S)-$ (L-21)

$-NH-(CH_2CH_2O)_{n2}-CH(CH_2OH)-$ (L-22)

$-NH-(CH_2CH_2O)_{n2}-CH_2-$ (L-23)

$-NH-(CH_2CH_2O)_{n2}-CH_2-CO-$ (L-24)

$-O-(CH_2)_{n3}-S-S-(CH_2)_{n4}-O-P(=O)_2-$ (L-25)

$-CO-(CH_2)_{n3}-O-CO-NH-(CH_2)_{n4}-$ (L-26)

$-CO-(CH_2)_{n3}-CO-NH-(CH_2)_{n4}-$ (L-27)

In formulas (L-4) to (L-21), n1 is an integer of 1 to 40, preferably 2 to 20, and more preferably 2 to 12.

In formulas (L-22) to (L-24), n2 is an integer of 1 to 20, preferably 1 to 10, and more preferably 1 to 6.

In formulas (L-25) to (L-27), n3 and n4 may be the same or different, and are an integer of 1 to 20, preferably 1 to 10, and more preferably 1 to 6.

Single-stranded DNA may be bound to either the left or right side of the linkers of formulas (L-1) to (L-27). Preferably, a double-stranded lipid is bound to the left side of the linker, and the 5'-end region of the sense strand of a double-stranded RNA is bound to the right side thereof.

The binding site of the double-stranded lipid and the linker may be suitably selected according to the types of double-stranded lipid and linker. Any position other than hydrophobic groups of the double-stranded lipid may be linked to the linker by a chemical bond. For example, when using a phosphatidylethanolamine, the linkage may be made by forming an amide bond, etc. between the amino group of phosphatidylethanolamine and the linker. When using a phosphatidylglycerol, the linkage may be made by forming an ester bond, an ether bond, etc. between the hydroxyl group of the glycerol residue and the linker. When using a phosphatidylserine, the linkage may be made by forming an amide bond or an ester bond, etc. between the amino group or carboxyl group of the serine residue and the linker. When using a phosphatidic acid, the linkage may be made by forming a phosphoester bond, etc. between the phosphate residue and the linker. When using a phosphatidylinositol, the linkage may be made by forming an ester bond, an ether bond, etc. between the hydroxyl group of the inositol residue and the linker.

The linker can be suitably selected according to the type of lipid to be linked. For example, when the double-stranded lipid is an amino group-containing phospholipid (e.g., phosphatidylethanolamine or phosphatidylserine), or a hydroxyl-containing phospholipid (e.g., phosphatidylglycerol or phosphatidylinositol), linkers of formulas (L-6), (L-7), (L-9), (L-10), (L-18), (L-26), and (L-27) are preferably used.

In addition to the above examples of linkers, other linkers such as N-succinimidyl-3-(2-pyridyldithio)propionate, N-4-maleimide butyric acid, S-(2-pyridyldithio)cysteamine, iodoacetoxysuccinimide, N-(4-maleimidebutyryloxy)succinimide, N-[5-(3'-maleimide propylamide)-1-carboxypentyl]iminodiacetic acid, N-(5-aminopentyl)iminodiacetic acid, and like bifunctional linkers (linkers containing two functional groups) are also usable.

The nucleotide of the sense strand to which either the double-stranded lipid or the linker used to link the double-stranded lipid is bound is not particularly limited, insofar as it is at least one of the first to sixth nucleotides from the 5' end of the sense strand. At least one of the first to fourth nucleotides from the 5' end is preferable. The first and/or second nucleotide from the 5' end are further preferable. The nucleotide at the 5' end (the first nucleotide from the 5' end) is particularly preferable.

The binding site of the sense strand to which the double-stranded lipid or the linker used for linking the lipid is bound is not particularly limited. The double-stranded lipid or the linker used for linking the double-stranded lipid is preferably bound to the sense strand by substitution of the hydrogen atom of the hydroxyl group of the phosphate portion of a specific nucleotide on the sense strand with the lipid or linker.

The number of double-stranded lipids bound to the double-stranded lipid-modified RNA of the invention is not particularly limited. For example, one to three double-stranded lipids, preferably one or two double-stranded lipids, and more preferably one double-stranded lipid may be bound.

The double-stranded lipid-modified RNA of the invention can be produced by synthesizing each of the above-mentioned sense strand having at least one double-stranded lipid bound thereto and the above-mentioned antisense strand, and hybridizing the sense and antisense strands according to a known method. A known method can also be used to produce the sense strand having a double-stranded lipid linked thereto.

Alternatively, the double-stranded lipid-modified RNA of the present invention can also be produced by synthesizing the above-mentioned sense and antisense strands according to known methods, hybridizing the sense and antisense strands into a double-stranded RNA, and then linking a double-stranded lipid to the 5' end of the sense strand of the double-stranded RNA by a known synthetic technique.

The double-stranded lipid-modified RNA of the invention can suppress or inhibit the expression of a target gene when introduced into cells. Therefore, the double-stranded lipid-modified RNA of the invention can be used as a pharmaceutical for suppressing the expression of a target gene or a pharmaceutical for gene therapy, or as an experimental material used to evaluate a suppressive effect on the expression of a target gene.

The cell into which the double-stranded lipid-modified RNA is introduced may be any cells derived from humans, nonhuman mammals, birds, insects, etc. Cells derived from humans or nonhuman mammals are preferable.

The method of introducing the double-stranded lipid-modified RNA into a cell may be the same as known methods for introducing siRNA. Any method that can bring an effective amount of the double-stranded lipid-modified RNA into contact with the target cell can be used. The introduction of the double-stranded lipid-modified RNA into a cell can be performed in vivo, in vitro, or ex vivo.

For example, in vivo introduction of the double-stranded lipid-modified RNA of the invention into cells can be performed by using a method comprising culturing cells in the presence of an appropriate amount of the double-stranded lipid-modified RNA. Further, in vitro or ex vivo introduction of the double-stranded lipid-modified RNA of the invention into cultured cells, cells derived from an organism, or tissues derived from an organism can be performed by incubating the cultured cells, cells derived from an organism, or tissues derived from an organism in the presence of the double-stranded lipid-modified RNA. Further, in vivo introduction of the double-stranded lipid-modified RNA of the invention into cells can be performed by administering the double-stranded lipid-modified RNA by direct insertion into tissues; intravenous, subcutaneous, intramuscular, interperitoneal, intraocular, digestive, or dental injection; inhalation administration into the nasal cavity, oral cavity, lungs, etc.; oral administration; transdermal administration through the skin; and transmucosal administration via the oral mucosa, vaginal mucosa, ocular mucosa, rectal mucosa, or uterine mucosa; etc.

The double-stranded lipid-modified RNA of the invention may be used in any amount that is effective for introducing the RNA into the target cell. The amount of the double-stranded lipid-modified RNA to be used may be, for example, 0.001 to 10 pmol (picomoles), preferably 0.001 to 1 pmol, and more preferably 0.01 to 0.1 pmol, per cell.

The double-stranded lipid-modified RNA of the invention has high ability to be delivered intracellularly, even when used alone. Therefore, the double-stranded lipid-modified RNA can be introduced into cells without using any known gene transfection reagents used for introducing siRNA into cells, or by using a known gene transfection reagent in a reduced amount.

The double-stranded lipid-modified RNA of the invention can suppress or inhibit the expression of a target gene, when it is introduced into a cell. Therefore, the double-stranded lipid-modified RNA can be used, for example, in the medicinal field to prevent, ameliorate, or treat a disease caused by the expression of the target gene. When the double-stranded lipid-modified RNA of the invention is used in the medicinal field, the double-stranded lipid-modified RNA is provided as a pharmaceutical composition produced by using the RNA and a pharmacologically acceptable carrier.

The pharmaceutically acceptable carrier to be used in the pharmaceutical composition is not particularly limited, and can be suitably selected according to the dosage form of the pharmaceutical composition. Examples of such carriers include aqueous carriers such as purified water, aqueous sugar solutions, buffers, physiological saline, aqueous polymer solutions and RNase-free water, excipients, etc.

The proportion of the double-stranded lipid-modified RNA in the pharmaceutical composition can be suitably selected from a range that allows the double-stranded lipid-modified RNA to be used in the above-mentioned amount. The proportion of the double-stranded lipid-modified RNA is, for example, 0.001 to 50 wt. %, preferably 0.01 to 10 wt. %, and more preferably 0.1 to 1 wt. %, based on the total amount of the pharmaceutical composition.

The dosage form of the pharmaceutical composition is not particularly limited, insofar as the double-stranded lipid-modified RNA can be introduced into cells. Examples of the dosage form include liquids (such as syrups), drops, injections, and like liquid formulations; lyophilized formulations, dry syrups, tablets, pills, powders, granules, capsules (such as soft capsules), and like solid formulations; etc. When the pharmaceutical composition of the invention is a solid preparation, the composition may be used in the form of a solution by adding distilled water for injection, sterile water, or the like, when used.

The target disease or condition for which the pharmaceutical composition of the invention is used is not particularly limited, insofar as the expression of the target gene is associated with the disease or condition. The relationship between the target gene and disease is known in this technical field.

The pharmaceutical composition of the invention can be introduced into human-derived cells to treat humans, or can be used to treat animals other than humans (non-human mammals).

EXAMPLES

The present invention is described in detail with reference to the following Examples; however, the invention is not limited to these Examples.

Example 1

Inhibitory Effects of 5' Double-Stranded Lipid-Modified RNAs on the Expression of the Luciferase Gene 1. Synthesis of Double-Stranded Lipid-Modified RNAs Targeting the Luciferase Gene
1-1. Sequences of Sense Strands and Antisense Strands Double-stranded RNAs of 21- and 27-base-long sense strands and 21- and 27-base-long antisense strands were designed so that they had sequences homologous to Renilla luciferase and were capable of suppressing the expression of the Renilla luciferase gene. The double-stranded RNAs formed were as follows: When a 21-base-long antisense strand and sense strand were used, a 21-base-long double-stranded RNA having a two-base dangling end at the 3' end was formed. When a 27-base-long antisense strand and sense strand were used, a 27-base-long double-stranded RNA in which both ends were blunt-ended was formed. The sequences of the RNAs used are as follows.

```
27nt dsRNA
Sense strand L27A:
                                           (SEQ ID NO: 1)
5'-CUGGCCUUUCACUACUCCUACGAGCAC-3'

Antisense strand L27B:
                                           (SEQ ID NO. 2)
3'-GACCGGAAAGUGAUGAGGAUGCUCGUG-5'

21nt siRNA
Sense strand L21A:
                                           (SEQ ID NO: 3)
5'-GGCCUUUCACUACUCCUACGA-3'

Antisense strand L21B:
                                           (SEQ ID NO. 4)
3'-GACCGGAAAGUGAUGAGGAUG-5'
```

The double-stranded RNAs were prepared using these sense strands and antisense strands. Each double-stranded RNA was prepared by mixing equimolar amounts of a single-stranded sense strand and antisense strand in a universal buffer (Hayashi Kasei Co., Ltd.), heating the mixture for 2 minutes at 92° C., and then gradually reducing the temperature to 4° C. The synthesized double-stranded RNAs were electrophoresed on a 20% polyacrylamide gel for 60 minutes at 250 V, and then confirmed by staining with a silver staining kit (GE Health Care Bioscience).

Of these double-stranded RNAs, the 21-base-long double-stranded RNA having a two-base dangling end at the 3' end is designated as "si L21A/L21B", and the 27-base-long double-stranded RNA in which both ends were blunt-ended is designated as "Ds L27A/L27B".

1-2. Synthesis of Double-Stranded Lipid-Modified RNAs Targeting the Luciferase Gene Double-stranded lipid-modified sense strands were synthesized by linking double-stranded lipids to the 5' ends of the sense strands of the double-stranded RNAs capable of suppressing the expression of the luciferase gene. In each of these double-stranded lipid-modified sense strands, a double-stranded lipid was covalently bound via an aminoalkyl group (Amino Modifier C6; Glen Research) linked to the 5' end of the sense strand. Each double-stranded lipid-modified sense strand was synthesized by reacting, in a liquid phase, a lipid compound containing an active ester group (hereinafter referred to as an "active ester-containing lipid compound") with a sense strand whose 5' end was modified by amination (Reaction Scheme 1 below).

Reaction Scheme 1

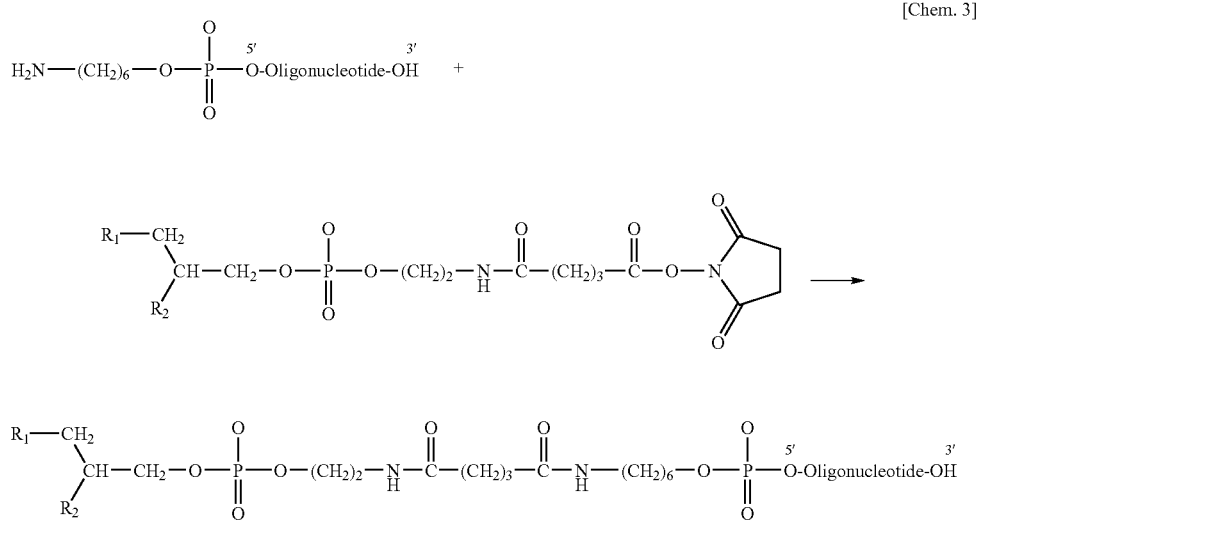

wherein $R_1$ and $R_2$ are the same or different, and each represent a fatty acid residue.

Figure 1:
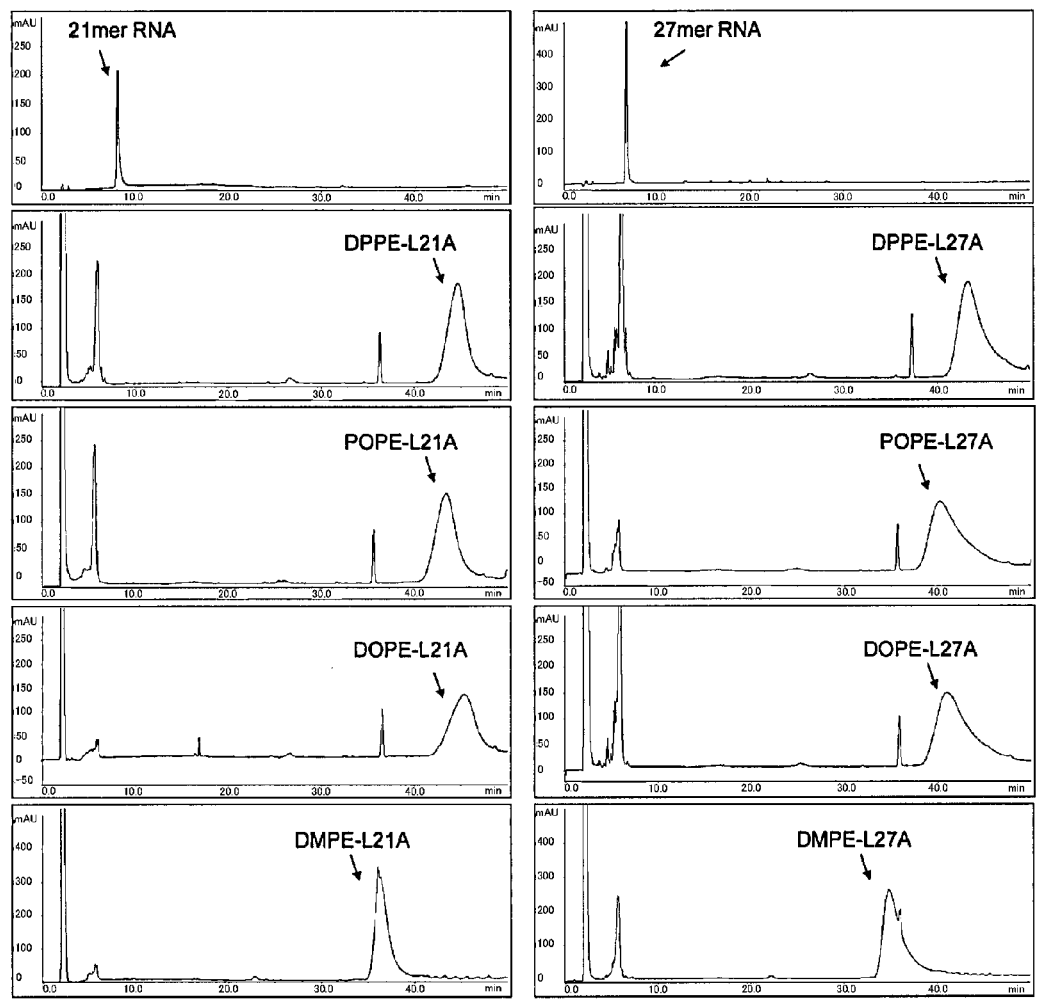
FIG. 1 shows the results of HPLC analysis performed on the double-stranded lipid-modified sense strands in Example 1.

A specific synthesis process is described below. In order to aminate the 5' end of the RNA, a conventional process (the phosphoramidite synthesis process) was performed using 5'-Amino-Modifier C6 (Glen Research) in RNA solid phase synthesis, thereby synthesizing a sense strand modified with an aminoalkyl group at the 5' end. The sense strand modified with an aminoalkyl group at the 5' end, which had already been purified by HPLC and subjected to MALDI-TOF MS analysis, was purchased from Hayashi Kasei Co., Ltd. In the resulting sense strand modified with an aminoalkyl group at the 5' end, $—(CH_2)_6—NH_2$ was linked to the 5' end (the phosphate residue of the first nucleotide from the 5' end). The concentration of the resulting single-stranded RNA was determined by measuring the absorbance at 260 nm using a UV spectrometer. The thus-obtained single-stranded RNA modified with an aminoalkyl group was mixed under condensation conditions with each of the following active ester-containing lipid derivatives [DPPE-NHS (N-(Succinimidyl-glutaryl)-L-α-Phosphatidylethanolamine, Dipalmitoyl); POPE-NHS (N-(Succinimidyl-glutaryl)-L-α-Phosphatidylethanolamine, 1-Palmitoyl-2-oleoyl); DOPE-NHS (N-(Succinimidyl-glutaryl)-L-α-Phosphatidylethanolamine, Dioleoyl); and DMPE-NHS; (N-(Succinimidyl-glutaryl)-L-α-Phosphatidylethanolamine, Dimyristoyl); all from NOF Corporation], which was dissolved in chloroform, thereby synthesizing a double-stranded lipid-modified sense strand. After the reaction, the reaction mixture was purified by HPLC in order to remove unwanted reagent in the reaction mixture containing the double-stranded lipid-modified sense strand. HPLC purification was performed with Buffer A: 100% 20 mM TEAA (pH 7.0) and Buffer B: 80% $CH_3CN$/20 mM TEAA (pH 7.0) at a linear gradient of 10-100% Buffer B over a period of 50 minutes. CAP CELL (4.6×150 mm, 5 μm; Shiseido) was used as the purification column. FIG. 1 shows exemplary HPLC analytical results. The double-stranded lipid-modified sense strand purified by HPLC was lyophilized and dissolved in purified water, after which the concentration and synthetic yield thereof were determined by UV spectral analysis.

The structures and yields of the synthesized double-stranded lipid-modified sense strands are shown below.

RNA (target: Luciferase)

Sense
L21A: 5'-GGCCUUUCACUACUCCUACGA-3'
SEQ ID NO: 3
L27A: 5'-CUGGCCUUUCACUACUCCUACGAGCAC-3'
SEQ ID NO: 1 si v21A/v21B RNA:

si Lipid-v21A/21B RNA:
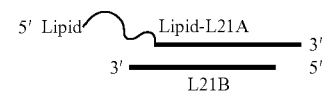

Antisense.
L21B: 5-GUAGGAGUAGUGAAAGGCCAG-3'
SEQ ID NO: 4
L27B: 5'-GUGCUCGUAGGAGUAGUGAAAGGCCAG-3'
SEQ ID NO: 2

Ds v27A/v27B RNA:

Ds Lipid-v27A/27B RNA:
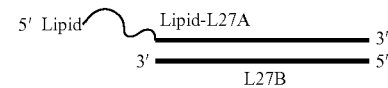

-continued

| | Yield (%) | |
|---|---|---|
| | 21 mer RNA | 27 mer RNA |
| DPPE-RNA (DPPE-L21A, DPPE-L27A) | 57.89 | 63.90 |
| POPE-RNA (POPE-L21A, POPE-L27A) | 48.62 | 59.44 |
| DOPE-RNA (DOPE-L21A, DOPE-L27A) | 64.45 | 79.49 |

| DMPE-RNA (DMPE-L21A, DMPE-L27A) | 45.97 | 18.40 |
|---|---|---|

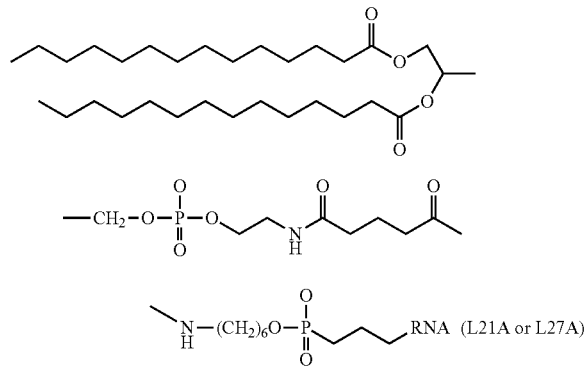

Each of the synthesized double-stranded lipid-modified sense strands was paired with an antisense strand to produce a double-stranded lipid-modified RNA. These double-stranded RNAs were formed according to the same procedure as described above, and confirmed by 20% polyacrylamide gel electrophoresis (see FIG. 2).

2. Degradative Enzyme Resistance of Double-Stranded Lipid-Modified RNAs

Figure 3:
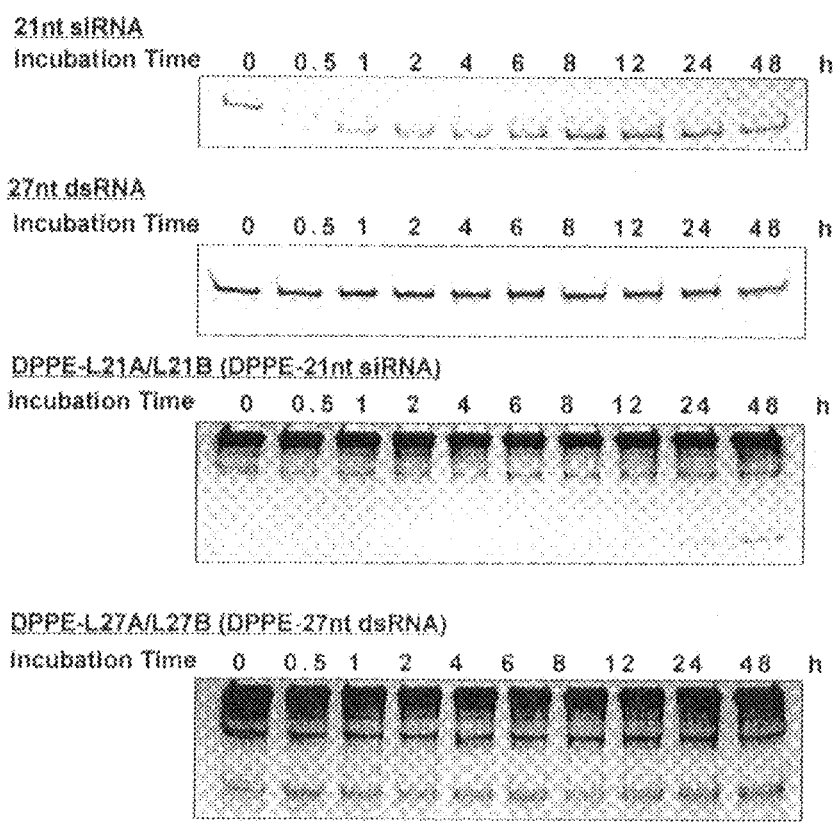
FIG. 3 shows the results of the investigation of the nuclease resistance of the double-stranded lipid-modified RNAs in Example 1.

The nuclease resistance of the double-stranded lipid-modified si L21A/L21B and Ds L27A/L27B was investigated. The experiments were performed as follows: Each of the double-stranded lipid-modified RNAs modified at the 5' end of the sense strand (si L21A/L21B and Ds L27A/L27B), adjusted to a final concentration of 2 μM, was incubated at 37° C. in an RPMI-1640 medium (Invitrogen) containing 10% FBS (Sanko Junyaku, Co., Ltd.) (final volume: 110 μl). After 0 h, 0.5 h, 1 h, 2 h, 4 h, 6 h, 8 h, 12 h, 24 h, and 48 h of incubation, a 10 μl aliquot of each RNA was taken out and inserted into a sample tube containing 2 μl of a loading die. In order to stop the degradation reaction, the sample taken was rapidly lyophilized in liquid nitrogen and preserved at −20° C. The resulting product was electrophoresed on a 20% polyacrylamide gel at 250 V for 70 minutes. The product was then stained with a silver staining kit (GE Health Care Bioscience) (see the product manual for staining conditions), and subjected to gel analysis on a Chemilmager 4000 (Alpha Innotech Corporation). As comparisons, the nuclease resistance of unmodified si L21A/L21B and Ds L27A/L27B was similarly evaluated. FIG. 3 shows the results of the gel electrophoresis.

As a result, the unmodified si L21A/L21B was rapidly digested in the serum-containing medium, and the disappearance of the sample RNA was confirmed in about 1 to 2 hours. In contrast, the double-stranded lipid-modified si L21A/L21B (si DPPE-L21A/L21B) exhibited very high nuclease resistance compared to si L21A/L21B, and the RNA survived even after 48 hours. The unmodified Ds L27A/L27B also exhibited high nuclease resistance, but the double-stranded lipid-modified Ds L27A/L27B (Ds DPPE-L27A/L27B) exhibited even higher nuclease resistance. Moreover, it was found that the degradative enzyme resistance of the double-stranded lipid-modified RNAs was improved because they were bound to serum proteins.

These results led to a new finding that the double-stranded lipid-modified RNAs possessed in vivo stability markedly higher than that of 21siRNAs that are generally in wide use.

Figure 4:
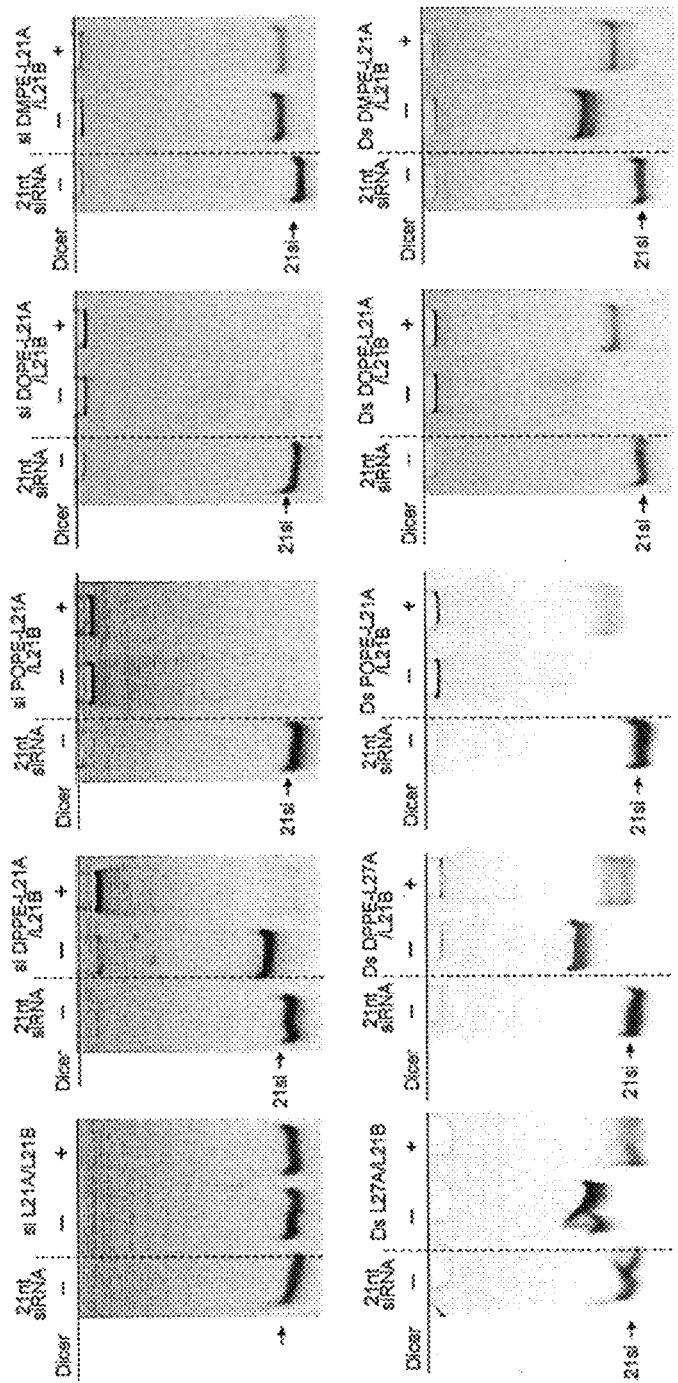
FIG. 4 shows the results of the investigation of Dicer processing of the double-stranded lipid-modified RNAs in Example 1.

3. Dicer Processing of the Double-Stranded Lipid-Modified RNAs Targeting the Luciferase Gene Processing of the synthesized RNAs and double-stranded lipid-modified RNAs by recombinant Dicer was investigated. The Dicer cleavage experiments were performed as follows: 10 μl of 0.5 U recombinant Dicer (Gene Therapy Systems) and each of the unmodified RNAs or double-stranded lipid-modified RNAs adjusted to a final concentration of 2 μM in a solution of 20 mM Tris-HCl (pH 8.0), 15 mM NaCl, and 2.5 mM MgCl$_2$ were prepared in sample tubes. The samples were incubated in an incubator at 37° C. for 12 hours. In order to subsequently stop the cleavage reactions by Dicer, 2 μl of Dicer Stop Solution (Gene Therapy Systems) was added into the reaction mixtures, followed by the addition of 2 μl of a loading die. The resulting sample products were electrophoresed on a 20% polyacrylamide gel at 250 V for 70 minutes. The products were then stained with a silver staining kit (GE Health Care Bioscience) (see the product manual for staining conditions), and subjected to gel analysis on a Chemilmager 4000 (Alpha Innotech Corporation). As a control, unmodified 21siRNA was also analyzed by gel electrophoresis. The results are shown in FIG. 4.

The results obtained showed that the unmodified Ds L27A/L27B was processed into 21-base-long RNAs by the action of Dicer; and that the 27-base-long double-stranded lipid-modified RNAs (Ds Lipid-L27A/L27B) were also processed into 21-base-long RNAs and other RNAs by the action of Dicer. These results have revealed that 27-base-long RNAs to which lipids are linked are recognized by Dicer, and undergo processing.

In contrast, it was found that the unmodified si L21A/L21B did not undergo Dicer processing, and that the double-stranded RNAs wherein the 21-base-long RNA was modified with double-stranded lipids (si Lipid-L21A/L21B) also did not undergo Dicer processing. Moreover, the double-stranded lipid-modified si L21A/L21B, when placed together with the Dicer protein, showed an increase in molecular weight, confirming the formation of a complex between the double-stranded lipid-modified si L21A/L21B and Dicer protein.

4. Suppression of Expression of the Luciferase Gene by Double-Stranded Lipid-Modified RNAs The RNA interference effects of the synthesized unmodified RNAs and double-stranded lipid-modified RNAs was assayed using Renilla luciferase as the target gene. HeLa cells (human cervical cancer cells; Institute of Development, Aging and Cancer, Tohoku University) adjusted to $1 \times 10^5$ cells/ml prior to the experiments were seeded on a 96-well plate at 100 µl per well, and incubated at 37° C. overnight. The next day, the old medium in the wells was removed, and a new, antibiotic-free medium was added at 80 µl per well; subsequently, 10 µl of a complex solution of a vector expressing firefly and Renilla luciferases (psiCHECK™-2 Vector; Promega) and Lipofectamine™ 2000 (trade name; Invitrogen) was added to each well containing the HeLa cells. The expression vector was adjusted to 0.02 µg per well, Lipofectamine™ 2000 was adjusted to 0.2 µl per well, and OptiMem (Invitrogen) was used to adjust the volume to a necessary level. To form a complex, the expression vector and Lipofectamine™ 2000 were mixed using OptiMem, and then the mixture was incubated at room temperature for 30 minutes. After the addition of the complex solution, the cells were incubated for 4 hours at 37° C. in the presence of 5% $CO_2$. After incubation, the unmodified double-stranded RNAs and the double-stranded lipid-modified RNAs obtained by introducing double-stranded lipids to the 5' ends of the sense strands, each containing an antisense sequence homologous to the gene sequence of the Renilla luciferase, were complexed with Lipofectamine™ 2000 (Invitrogen) at final concentrations of 0 nM, 0.2 nM, 0.5 nM, 1 nM, 2 nM, 5 nM, and 10 nM; and 10 µl each of the resulting complex solutions was added to the HeLa cells into which the expression vector had been introduced. The final volume per well was 100 µl. The complex solution of each RNA and Lipofectamine™ 2000 was prepared by mixing the aqueous RNA solution at 5 µl per well and an OptiMem solution of Lipofectamine™ 2000 (0.2 µl) at 5 µl per well, and incubating the mixture at room temperature for 30 minutes. After the introduction of RNA, the cells were incubated for 48 hours, and the levels of firefly and Renilla luciferase expression were assayed using a Dual-Glo™ Luciferase Assay System (Promega) and a luminometer (MicroLumat LB96p; Berthold), and the suppressing effects on the Renilla luciferase expression were determined based on the level of firefly luciferase expression as a control.

Figure 5:
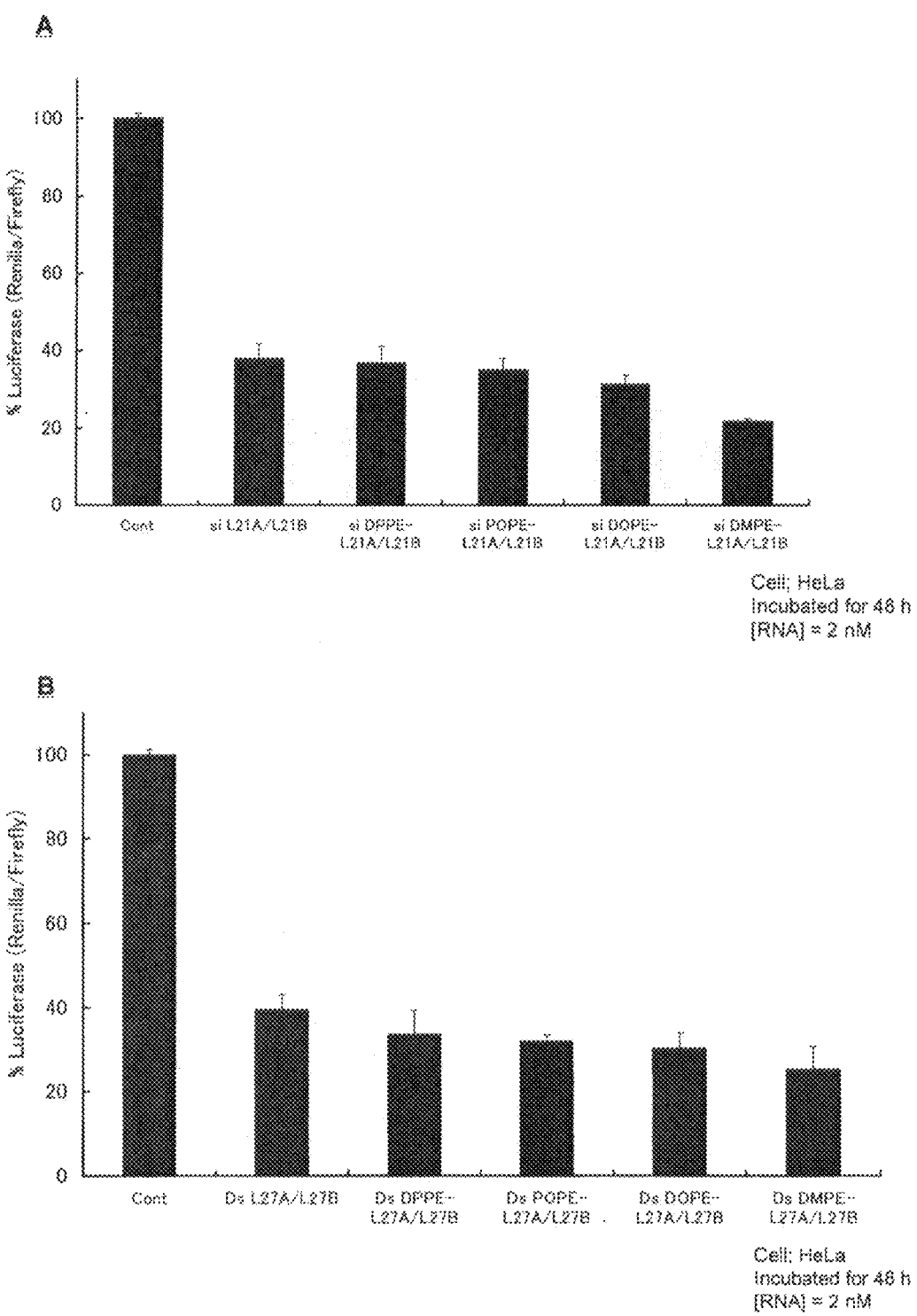
FIG. 5 shows the results of the investigation of the RNA interference effects of the double-stranded lipid-modified 27 nt dsRNAs at a concentration of 2 nM in Example 1.

The results are shown in FIG. 5. In FIG. 5, Graph A shows the results of suppression on luciferase gene expression using the double-stranded lipid-modified 21 nt siRNAs; and Graph B shows the results of suppression on luciferase gene expression using the double-stranded lipid-modified 27 nt dsRNAs. The unmodified 21 nt siRNA and 27 nt dsRNA were also evaluated. The results confirmed that the 21 nt siRNAs and 27 nt dsRNAs to which double-stranded lipids were linked demonstrated RNA interference effects markedly higher than those of the unmodified 21 nt siRNA and 27 nt dsRNA.

Example 2

Inhibitory Effects of 5' Double-Stranded Lipid-Modified RNAs on VEGF Gene Expression 1. Synthesis of Double-Stranded Lipid-Modified RNAs Targeting the VEGF Gene 1-1. Sequences of Sense Strands and Antisense Strands Double-stranded RNAs of 27- and 21-base-long sense strands and 27- and 21-base-long antisense strands were designed such that they had sequences homologous to VEGF (vascular endothelial growth factor) and were capable of suppressing the expression of the VEGF gene. The following experiments were conducted using these double-stranded RNAs. Note that 21siRNA is a double-stranded RNA having two-base dangling ends at the 3' ends of both of the sense strand and antisense strand; and 27 nt dsRNA is a completely double-stranded RNA having no dangling ends (single-stranded regions), i.e., a double-stranded RNA in which both of the 5' and 3' ends of the sense strand are blunt-ended. The sequences of the 27 nt dsRNA and 21siRNA used are as follows.

```
27nt dsRNA
Sense strand v27A:
                                    (SEQ ID NO: 5)
5'-CUUCCUACAGCACAACAAAUGUGAAUG-3'

Antisense strand v27B:
                                    (SEQ ID NO: 6)
3'-GAAGGAUGUCGUGUUGUUUACACUUAC-5'

21nt siRNA
Sense strand v21A:
                                    (SEQ ID NO: 7)
5'-UCCUACAGCACAACAAAUGUG-3'

Antisense strand v21B:
                                    (SEQ ID NO: 8)
3'-GAAGGAUGUCGUGUUGUUUAC-5'
```

These sense strands and antisense strands were annealed in the same manner as in Example 1 to form double strands, thereby producing double-stranded lipid-unmodified RNAs. The formation of the double strands was confirmed by 20% acrylamide gel electrophoresis, according to the same procedure as Example 1.

1-2. Synthesis of Double-Stranded Lipid-Modified RNAs Targeting the VEGF Gene

Figure 6:
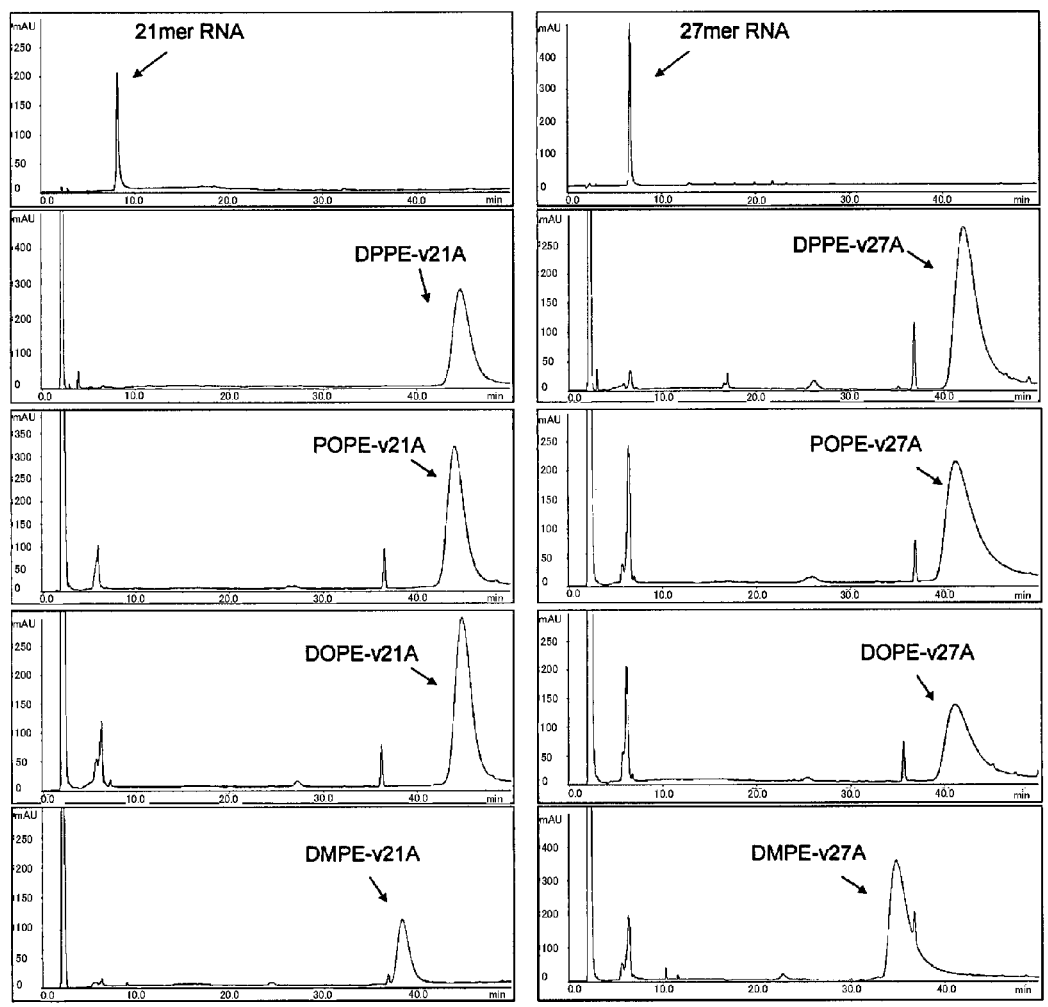
FIG. 6 shows the results of HPLC analysis performed on the double-stranded lipid-modified sense strands in Example 2.

Double-stranded lipid-modified RNAs were synthesized by linking lipids to the 5' ends of the sense strands of the above-mentioned double-stranded RNAs capable of suppressing the expression of the VEGF gene. In each of the double-stranded lipid-modified RNAs, a double-stranded lipid was covalently bound via an aminoalkyl group (Amino Modifier C6; Glen Research) linked to the 5' end of the sense strand. Double-stranded lipid-modified single-stranded RNAs (sense strands) were synthesized according to the same procedure as in Example 1. FIG. 6 shows the results of HPLC on the synthesized double-stranded lipid-modified sense strands. The elution times for the double-stranded lipid-modified sense strands targeting the VEGF gene were also substantially the same as in Example 1.

The structural models and yields of the double-stranded lipid-modified RNAs targeting the VEGF gene are as follows.

RNA (Target: VEGF)

Sense
v21A: 5'-UCCUACAGCACAACAAAUGUG-3' (v21A)
SEQ ID NO: 7
v27A 5'-CUUCCUACAGCACAACAAAUGUGAAUG-3' (v27A)
SEQ ID NO: 5

Antisense
v21B: 5'-CAUUUGUUGUGCUGUAGGAAG-3'
SEQ ID NO: 8
v27B: 5'-CAUUCACAUUUGUUGUGCUGUAGGAAG-3'
SEQ ID NO: 6 si v21A/v21B RNA:
5'────v21A────3'
3'────v27B────5'

Ds v27A/v27B RNA:
5'────v27A────3'
3'────v27B────5' si Lipid-v21A/21B RNA:
5' Lipid⌒Lipid-v21A 3'
3'────v21B────5'

Ds Lipid-v27A/27B RNA:
5' Lipid⌒Lipid-v27A 3'
3'────v27B────5'

| | Yield (%) | |
|---|---|---|
| | 21 mer RNA | 27 mer RNA |
| DPPE-RNA (DPPE-v21A, DPPE-v27A) | 77.59 | 61.51 |
| POPE-RNA (POPE-v21A, POPE-v27A) | 81.15 | 63.28 |
| DOPE-RNA (DOPE-v21A, DOPE-v27A) | 56.32 | 66.68 |

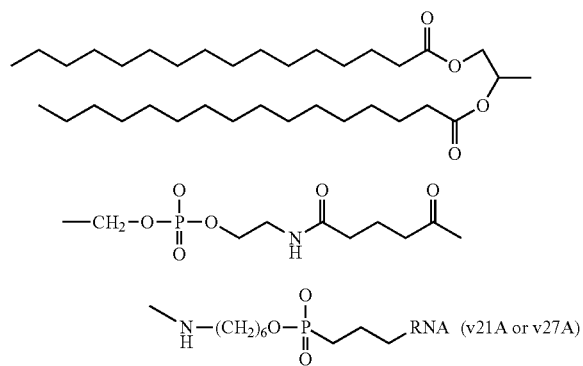

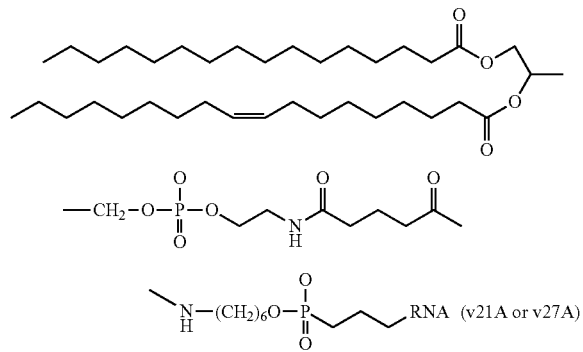

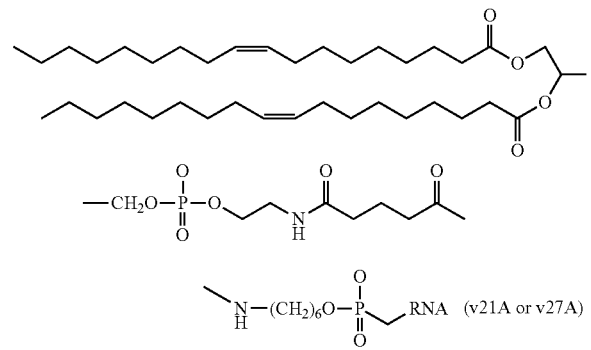

| DMPE-RNA (DMPE-v21A, DMPE-v27A) | 61.59 | 57.30 |

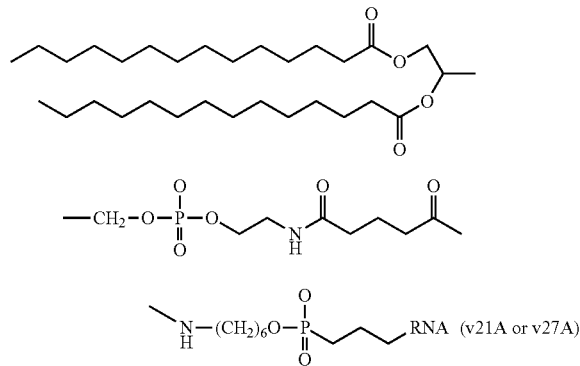

Figure 7:
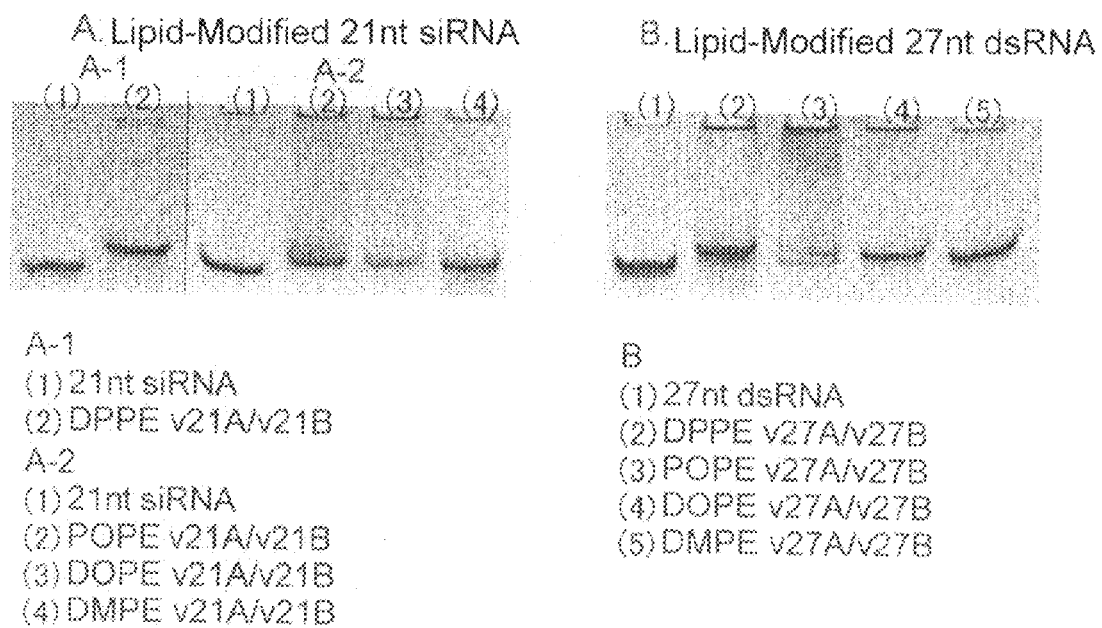
FIG. 7 shows the results of confirming the formation of the double strands of the double-stranded lipid-modified RNAs in Example 2.

The synthesized double-stranded lipid-modified sense strands were paired with antisense strands to produce double-stranded lipid-modified RNAs. The formation of the double stranded RNAs was confirmed by 20% polyacrylamide gel electrophoresis according to the same procedure as in Example 1 (see FIG. 7).

2. Degradative Enzyme Resistance of Double-Stranded Lipid-Modified RNAs

Figure 8:
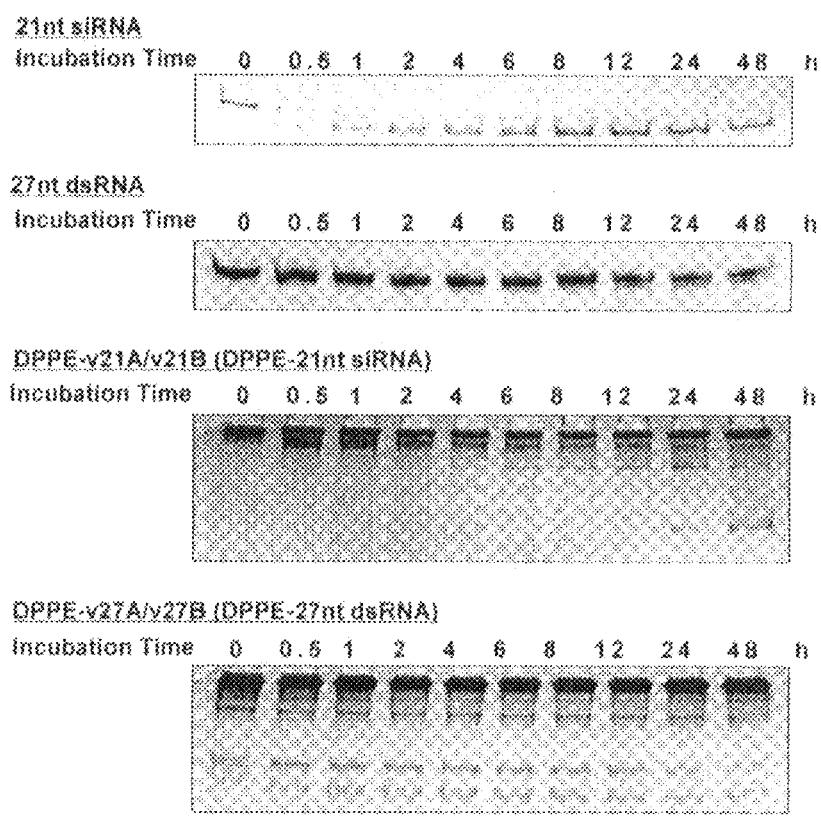
FIG. 8 shows the results of the investigation of the nuclease resistance of the double-stranded lipid-modified RNAs in Example 2.

The nuclease resistance of the double-stranded lipid-modified si v21A/v21B and Ds v27A/v27B was investigated. As comparisons, the nuclease resistance of unmodified si L21A/L21B and Ds L27A/L27B was also evaluated. The experiments were conducted according to the same method as in Example 1. FIG. 8 shows the results of gel electrophoresis.

According to the results, the unmodified si v21A/v21B was rapidly digested in the serum-containing medium, and the disappearance of the sample RNA was confirmed in about 1 to 2 hours. In contrast, the double-stranded lipid-modified si v21A/v21B (si DPPE-v21A/v21B) exhibited very high nuclease resistance compared to si v21A/v21B, and the RNA survived even after 48 hours. The unmodified Ds v27A/v27B also exhibited high nuclease resistance, but the double-stranded lipid-modified Ds v27A/v27B (Ds DPPE-v27A/v27B) exhibited even higher nuclease resistance. Moreover, it was found that the degradative enzyme resistance of the double-stranded lipid-modified RNAs was improved because they were bound to serum proteins.

These results also revealed that the double-stranded lipid-modified RNAs possessed in vivo stability markedly higher than that of 21siRNAs that are generally in wide use.

Figure 9:
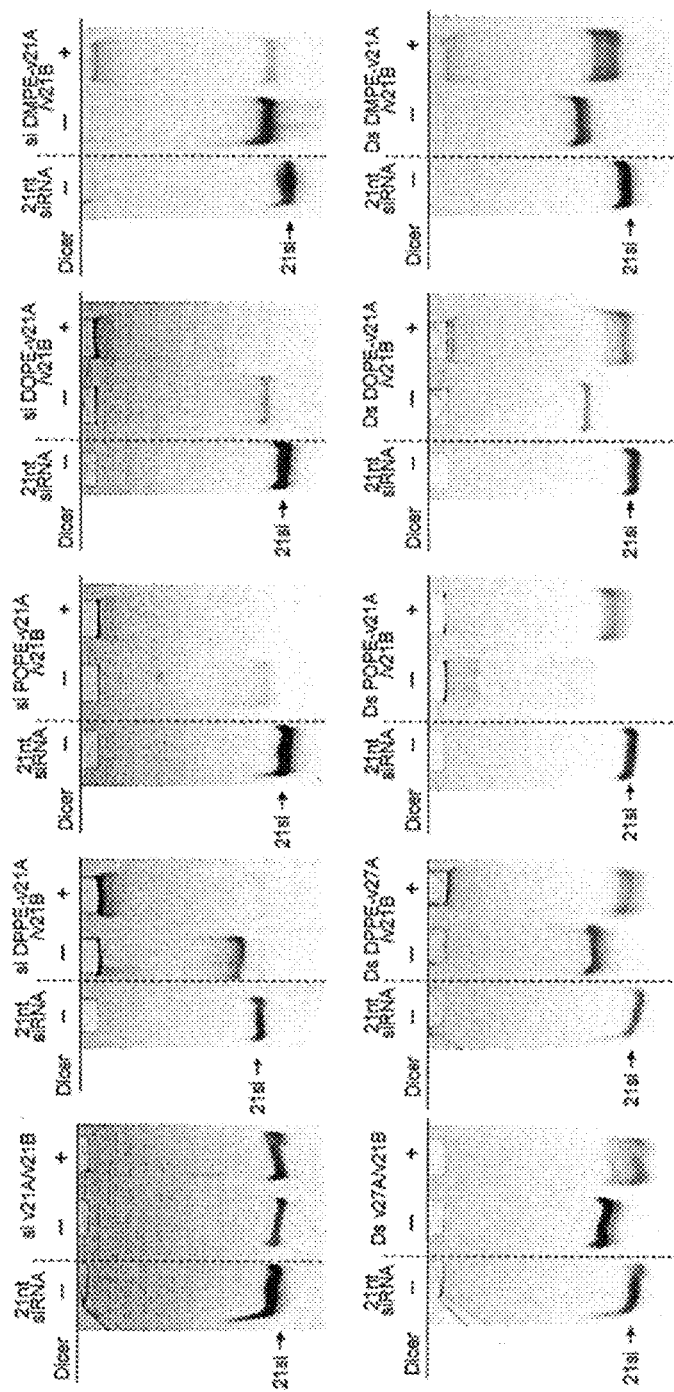
FIG. 9 shows the results of the investigation of the Dicer processing of the double-stranded lipid-modified RNAs in Example 2.

3. Dicer Processing of the Double-Stranded Lipid-Modified RNAs Targeting the VEGF Gene Processing of the synthesized double-stranded lipid-unmodified RNAs and double-stranded lipid-modified RNAs by recombinant Dicer was investigated. The Dicer cleavage experiments were performed according to the same procedure as in Example 1. The results are shown in FIG. 9.

The results obtained showed that the unmodified Ds v27A/v27B was processed into 21-base-long double-stranded RNAs by the action of Dicer; and that the 27-base-long double-stranded lipid-modified RNAs (Lipid-Ds v27A/v27B) were also processed into 21-base-long RNAs and other RNAs by the action of Dicer. These results revealed that 27-base-long RNAs to which lipids are linked are recognized by Dicer, and undergo processing.

In contrast, it was found that the unmodified si v21A/v21B did not undergo Dicer processing, and that the RNAs wherein the 21-base-long double-stranded RNA was modified with double-stranded lipids also did not undergo Dicer processing.

Moreover, the double-stranded lipid-modified si v21A/v21B, when placed together with the Dicer protein, showed an increase in molecular weight, confirming the formation of a complex between the double-stranded lipid-modified si L21A/L21B and Dicer protein.

4. Suppression of VEGF Gene Expression by Double-Stranded Lipid-Modified RNAs

An evaluation of inhibitory effects on VEGF gene expression, using HeLa cells (human cervical cancer cells; Institute of Development, Aging and Cancer, Tohoku University), and A549 cells (human lung cancer cells; Institute of Development, Aging and Cancer, Tohoku University) was performed on si v21A/v21B with unmodified ends, Ds v27A/v27B with unmodified ends, si v21A/v21B (si Lipid-v21A/v21B) modified with double-stranded lipids at the 5' ends of the sense strands, and Ds v27A/v27B (Ds Lipid-v27A/v27B) modified with double-stranded lipids at the 5' ends of the sense strands. The same evaluation was also conducted on RNAs (27 nt dsRNA (Random), 21 nt siRNA (Random)) not having a gene sequence homologous to the VEGF gene.

The experiments were performed according to the following procedures. Each of HeLa cells and A549 cells, adjusted to $1 \times 10^5$ cells/ml prior to the experiments, were seeded on a 24-well plate at 500 µl per well, and incubated at 37° C. overnight. The next day, the old medium in the well was removed, and a fresh, antibiotic-free medium was added at 450 µl per well. MEM medium was used for the HeLa cells, and PRMI-1640 medium was used for the other cells. A complex of the Lipofectamine™ 2000 (Invitrogen) solution (25 µl) with each of the unmodified RNAs or double-stranded lipid-modified RNA (25 µl) containing an antisense sequence homologous to the gene sequence of VEGF was formed, and then 50 µl of the resulting RNA solution was added to 450 µl of the above-mentioned cells. The final volume per well was 500 µl. The complex solution of each RNA and Lipofectamine™ 2000 was prepared by mixing the aqueous RNA solution at 25 µl per well and an OptiMem solution of Lipofectamine™ 2000 (2 µl) at 25 µl per well, and incubating the mixture at room temperature for 30 minutes. After the RNA introduction, the cells were incubated for 48 hours at 37° C. in the presence of 5% $CO_2$. After incubation, the cells were washed with PBS (−) three times, and the total RNA in the cells was extracted using an RNeasy Plus Mini Kit (Qiagen). RT-PCR reactions were subsequently performed to measure the amount of mRNA of the VEGF. A Qiagen OneStep RT-PCR Kit (Qiagen) was used for the RT-PCR reaction, and 5'-CCC TGA TGA GAT CGA GTA CAT CTT-3' (SEQ ID NO: 9) and 5'-ACC GCC TCG GCT TGT CAC-3' (SEQ ID NO: 10) were used as the PCT primers for VEGF. As a control, the GAPDH gene was measured according to the same procedure. 5'-GGAAAGCTGTGGCGTGATG-3' (SEQ ID NO: 11) and 5'-CTGTTGCTGTAGCCGTATTC-3' (SEQ ID NO: 12) were used as the primers for GAPDH. The RT-PCR reactions were performed as follows. The RT (Reverse Transcription) reaction was performed at 50° C. for 30 minutes, and a PCR reaction, involving repeated 25 to 28 cycles (depending on the cells used) of a double-strand separation reaction at 92° C. for 30 seconds, an annealing reaction at 55° C. for 30 seconds, and an elongation reaction at 68° C. for 45 seconds, was performed. Lastly, incubation was performed at 68° C. for 10 minutes, the temperature was decreased to 4° C., and the reaction was completed. The reagents, total RNA, primers, and the like used in RT-PCR were prepared according to the reaction conditions of the Qiagen OneStep RT-PCR Kit (Qiagen). After the RT-PCR reactions, 2 µl of a loading die was added, and the RT-PCR products derived from the mRNAs of VEGF and GAPDH were confirmed using 2% agarose gel. The suppressing effects on gene expression were evaluated by measuring the level of VEGF expression in the cells into which the RNAs (both unmodified RNAs and double-stranded lipid-modified RNAs) were introduced, taking the level of expression of the VEGF gene in control cells (the cells into which the double-stranded RNAs were not introduced) as 100%. The error in the levels of expression among the cells was corrected based on the level of gene expression of the control gene (GAPDH).

Figure 10:
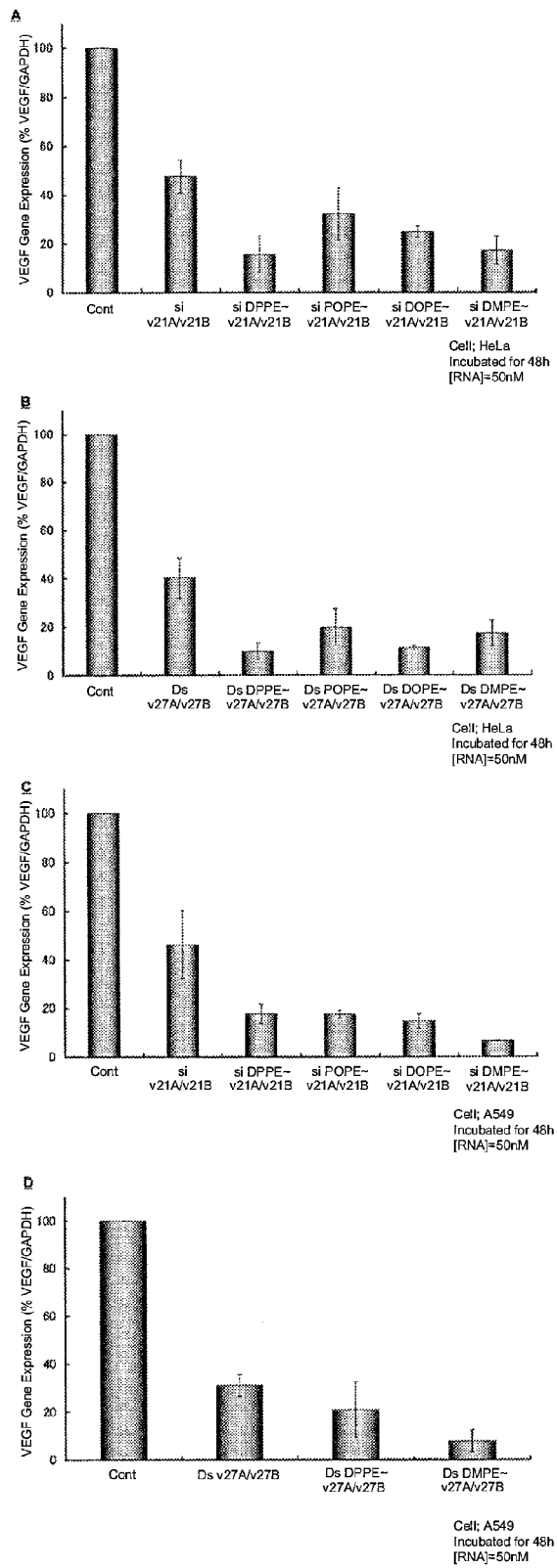
FIG. 10 shows the results of the investigation of the RNA interference effects of the double-stranded lipid-modified RNAs on the VEGF gene in HeLa cells and A549 cells in Example 2.

FIG. 10 shows the results of the RNA interference effects of the unmodified RNAs and double-stranded lipid-modified RNAs targeting VEGF at an RNA concentration of 50 nM. FIGS. 10A and 10B are graphs showing the suppressing effects on VEGF gene expression of the unmodified RNAs and double-stranded lipid-modified RNAs in HeLa cells; and FIGS. 10C and 10D are graphs showing the suppressing effects on VEGF gene expression of the unmodified RNAs and double-stranded lipid-modified RNAs in A549 cells. In Graphs A and C, 21-base-long double-stranded RNAs are used; and in Graphs B and D, 27-base-long double-stranded RNAs are used.

As a result, the observation of the abilities of the double-stranded lipid-modified si v21A/v21B to suppress gene expression in HeLa cells (Graph A) showed that all of the double-stranded lipid-modified RNAs had abilities to suppress gene expression higher than that of the unmodified RNA. In particular, si DPPE-v21A/v21B exhibited a very high ability to suppress gene expression. Similarly, the observation of the abilities of the double-stranded lipid-modified Ds v27A/v27 to suppress gene expression in HeLa cells (Graph B) showed that all of the double-stranded lipid-modified RNAs had abilities to suppress gene expression higher than that of the unmodified RNA. In particular, Ds DPPE-v27A/v27B exhibited a very high ability to suppress gene expression.

The observation of the abilities of the lipid-modified si v21A/v21B to suppress VEGF gene expression in A549 cells (Graph C) showed that all of the double-stranded lipid-modified RNAs had abilities to suppress gene expression higher than that of the unmodified RNA. In particular, si DPPE-v21A/v21B exhibited a very high ability to suppress gene expression. The observation of the abilities of the double-stranded lipid-modified Ds v27A/v27 to suppress gene expression in A549 cells (Graph D) showed that the RNAs to which DPPE or DMPE was linked exhibited abilities to suppress gene expression higher than that of the unmodified RNA.

These results revealed that the 21-base-long and 27-base-long siRNAs and dsRNAs wherein double-stranded lipids were covalently bound to the 5' ends of the sense strands of the double-stranded RNAs exhibited abilities to suppress gene expression higher than that of each of the unmodified double-stranded RNAs. In particular, the double-stranded RNAs to which DPPE was linked exhibited a very high ability to suppress gene expression. Additionally, the RNAs to which DMPE or DOPE was linked also exhibited high abilities to suppress gene expression, as compared to the unmodified RNA.

The VEGF-targeting double-stranded RNAs used herein were demonstrated to suppress the expression of the target gene in a highly sequence-specific manner. Moreover, the test results suggested that side effects upon the cells were reduced by linking the double-stranded lipids to the double-stranded RNAs.

5. Investigation of the Cellular Uptake Efficiencies of Lipid-Modified Double-Stranded RNAs Each of HeLa cells (human cervical cancer cells; Institute of Development, Aging and Cancer, Tohoku University) and A549 cells (human lung cancer cells; Institute of Development, Aging and Cancer, Tohoku University), adjusted to $1 \times 10^5$ cells/ml prior to the experiments, were seeded on 24-well plates at 1 ml per well, and the cells were incubated in a medium containing 10% fetal bovine serum (FBS; Sanko Junyaku, Inc.) and antibiotics at 37° C. in the presence of 5% $CO_2$. As the antibiotics and media, MEM medium (Invitrogen) was used for the HeLa cells, and RPMI-1640 (Invitrogen) was used for the other cells. Prior to the introduction of fluorescently labeled double-stranded lipid-modified RNAs, these media were replaced with an antibiotic-free medium (450 µl). The fluorescently labeled double-stranded lipid-modified RNAs were obtained by using 21 nt and 27 nt antisense strands labeled with 6-FAM at the 5' ends, and pairing the thus-labeled 21 nt and 27 nt antisense strands with unmodified 21 nt and 27 nt sense strands, respectively, and with 21 nt and 27 nt sense strands modified with double-stranded lipids at the 5' ends, respectively, to form double-strands. The cellular uptake experiments were performed as follows. To form a complex of each fluorescently labeled double-stranded lipid-modified RNA and Lipofectamine™ 2000 (Invitrogen), 25 µl of a mixed solution of 10 µl of each 10 µM aqueous fluorescently labeled oligonucleotide solution and 15 µl of the OptiMem solution were combined with 25 µl of a mixed solution of 2 µl of the Lipofectamine™ 2000 (Invitrogen) solution and 23 µl of the OptiMem solution to form a 50 µl mixed solution, and the mixed solution was incubated at room temperature for 30 minutes. The resulting 50 µl of the fluorescently labeled oligonucleotide complex was added to 450 µl of the cells prepared above (the final concentration of the double-stranded RNAs: 200 nM), and incubated for 4 hours at 37° C. in the presence of 5% $CO_2$. The cells were subsequently washed with PBS (−) or the medium three times, and the cellular uptake of the double-stranded RNAs was evaluated using a confocal fluorescence laser microscope and flow cytometry.

A Radiance 2000 system (Bio Rad) was used as a confocal fluorescence laser microscope, and fluorescence was observed using an argon laser. Flow cytometry was performed by using a Coulter EPICS XL cytometer (Beckman Coulter) to measure cellular uptake efficiency per 10,000 cells. XL EXPO32™ software (Beckman Coulter) was used in the flow cytometric analysis.

The results are shown in FIG. 11. Sections A and B of FIG. 11-1 show the results obtained by measuring the cellular uptake efficiencies when fluorescently labeled 21-base-long and 27-base-long (si v21A/v21B and si v27A/v27B) RNAs, and fluorescently labeled RNAs modified with double-stranded lipids at the 5' ends of the sense strands, were introduced into HeLa cells using Lipofectamine™ 2000 as a transfection reagent. Section C and D of FIG. 11-2 show the results obtained by measuring the cellular uptake efficiencies when fluorescently labeled 21-base-long and 27-base-long (si v21A/v21B and si v27A/v27B) RNAs, and fluorescently labeled RNAs modified with double-stranded lipids at the 5' ends of the sense strands, were introduced into A549 cells using Lipofectamine™ 2000 as a transfection reagent.

The results confirmed the introduction of the unmodified RNAs and double-stranded lipid-modified RNAs into both of the cells (HeLa cells and A549 cells) in the presence of Lipofectamine™ 2000. In particular, the observations by confocal fluorescence laser microscopy and flow cytometry showed that the 27-base-long RNAs modified with double-stranded lipids at the 5' ends of the sense strands exhibited very high cellular uptake efficiencies, compared to the unmodified RNAs. Moreover, the observation by confocal fluorescence laser microscopy indicated that the double-stranded lipid-modified RNAs were actively localized into the cytoplasm. In particular, the 27-base-long double-stranded RNAs to which DPPE or DMPE was linked as a double-stranded lipid exhibited excellent cellular uptake efficiencies.

The results also confirmed that the double-stranded lipid-modified RNAs wherein double-stranded lipids were linked to the 21-base-long RNA exhibited high cellular uptake efficiencies in the presence of Lipofectamine™ 2000. In particular, the 21-base-long RNA to which DMPE was linked as a double-stranded lipid was confirmed to have an excellent cellular uptake efficiency.

These results led to a new finding that when a lipid is covalently bound to the 5' end of the sense strand of a double-stranded RNA, the double-stranded RNA can demonstrate dramatically improved cellular uptake efficiency, and can also be localized into the cytoplasm of cells.

Example 3

Synthesis of Double-Stranded Lipid-Modified RNAs Targeting the WT1 Gene

Using a technique different from that of Examples 1 and 2, a double-stranded lipid-modified sense strand was synthesized by linking a double-stranded lipid to the 5' end of the sense strand of a double-stranded RNA capable of suppressing the expression of the WT1 gene.

First, a sense strand and an antisense strand were prepared according to a known method. Subsequently, aminoalkylation of the 5' end of the sense strand was performed according to a conventional process (the phosphoramidite synthesis process) using 5'-Amino-Modifier C6 (Glen Research), thereby synthesizing a sense strand modified with an aminoalkyl group at the 5' end. In the synthesized sense strand modified with an aminoalkyl group at the 5' end, —$(CH_2)_6$—$NH_2$ was linked via an oxygen atom to the phosphate residue of the first nucleotide from the 5' end. The synthesized sense strand modified with an aminoalkyl group at the 5' end was paired with an antisense strand to produce a double-stranded RNA (hereinafter referred to as the "aminoalkyl-modified double-stranded RNA"). The double-stranded RNA was formed according to the same procedure as described above. The thus-obtained aminoalkyl-modified double-stranded RNA was mixed with an active ester-containing double-stranded lipid derivative (DPPE-NHS (N-(Succinimidyl-glutaryl)-L-α-Phosphatidylethanolamine, Dipalmitoyl); from NOF Corporation) dissolved in chloroform under condensation conditions, to synthesize a double-stranded lipid-modified RNA (DPPE-modified double-stranded RNA). After the reaction, the reaction mixture was purified by HPLC to remove unwanted reagent in the reaction mixture containing the double-stranded lipid-modified RNA. HPLC purification was performed with Buffer A: 100% 20 mM TEAA (pH 7.0) and Buffer B: 80% $CH_3CN$/20 mM TEAA (pH 7.0) at a linear gradient of 10-100% Buffer B over a period of 50 minutes. CAP CELL (4.6×150 mm, 5 μm; Shiseido) was used as the purification column. FIG. 12 shows exemplary HPLC analytical results. The HPLC-purified double-stranded lipid-modified RNA was lyophilized and dissolved in purified water, after which the concentration and synthetic yield thereof were determined by UV spectral analysis. The double-stranded lipid-modified RNA was confirmed by 20% polyacrylamide gel electrophoresis (FIG. 13).

The structure and yield of the synthesized double-stranded RNA are shown below.

Unmodified Double-Stranded RNA (WT-1)

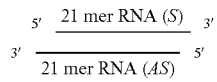

Aminoalkyl-Modified Double-Stranded RNA (WT-1-$NH_2$)

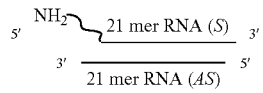

DPPE-Modified Double-Stranded RNA (WT-1-DPPE)

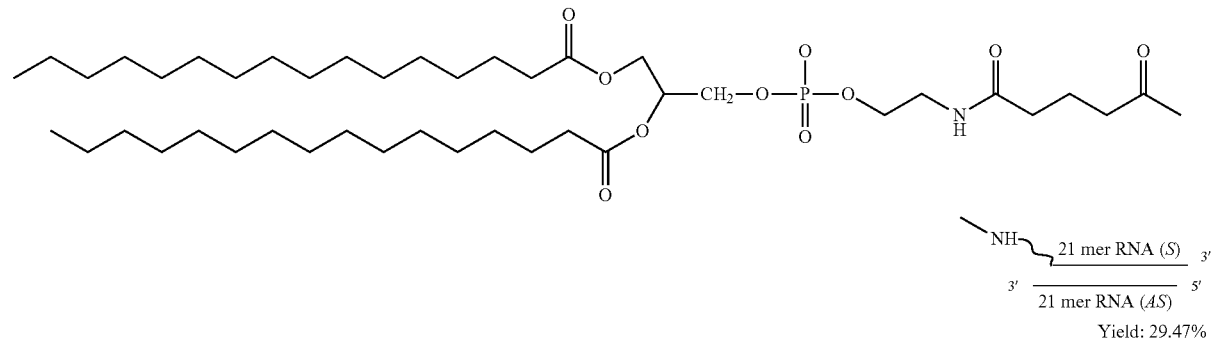

Yield: 29.47%

The invention claimed is:

1. A double-stranded lipid-modified RNA comprising an antisense strand having a nucleotide sequence complementary to a target sequence in a target gene, and a sense strand having a nucleotide sequence complementary to the antisense strand, the double-stranded lipid modified RNA being capable of suppressing expression of the target gene, and the sense strand having a double-stranded lipid bound directly or via a linker to at least one of the first to sixth nucleotides from the 5' end, wherein said RNA does not contain any other nucleotide modifications, and
   wherein said double-stranded lipid is a glycerophospholipid, and wherein said glycerophospholipid comprises two hydrophobic groups which each comprise a fatty acid residue.

2. The double-stranded lipid-modified RNA according to claim 1, which is blunt-ended on the 5'-end side of the sense strand, and is blunt-ended or has a dangling end on the 3'-end side of the sense strand.

3. The double-stranded lipid-modified RNA according to claim 1, which has dangling ends on both the 5'- and 3'-end sides of the sense strand.

4. The double-stranded lipid-modified RNA according to claim 1, wherein the sense strand consists of 21 to 27 nucleotides.

5. The double-stranded lipid-modified RNA according to claim 2, which is blunt-ended on both the 5'- and 3'-end sides of the sense strand, each of the sense and antisense strands consisting of 27 nucleotides.

6. The double-stranded lipid-modified RNA according to claim 2, which is blunt-ended on both the 5'- and 3'-end sides of the sense strand, each of the sense and antisense strands consisting of 23 nucleotides.

7. The double-stranded lipid-modified RNA according to claim 2, which is blunt-ended on the 5'-end side of the sense strand, the sense strand consisting of 25 nucleotides, and the antisense strand consisting of 23 nucleotides.

8. The double-stranded lipid-modified RNA according to claim 3, wherein each of the sense and antisense strands consists of 21 nucleotides.

9. The double-stranded lipid-modified RNA according to claim 1, wherein two hydrophobic groups of the double-stranded lipid are the same or different, and each is a saturated or unsaturated fatty acid residue having 6 to 50 carbon atoms.

10. The double-stranded lipid-modified RNA according to claim 1, wherein the double-stranded lipid is phosphatidylethanolamine.

11. The double-stranded lipid-modified RNA according to claim 10, wherein the double-stranded lipid is at least one member selected from the group consisting of dimyristoylphosphatidylethanolamine, dipalmitoylphosphatidylethanolamine, 1-palmitoyl-2-oleyl-phosphatidylethanolamine, and dioleoylphosphatidylethanolamine.

12. The double-stranded lipid-modified RNA according to claim 1, wherein the lipid is bound to at least one of the first to sixth nucleotides from the 5' end of the sense strand via a linker represented by the formula (L-27)

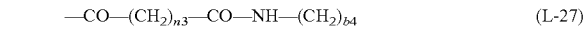

$$-CO-(CH_2)_{n3}-CO-NH-(CH_2)_{n4} \qquad (L-27)$$

wherein n3 and n4 are the same or different, and each represents an integer of 1 to 20.

13. A pharmaceutical composition comprising the double-stranded lipid-modified RNA of claim 1, and a pharmaceutically acceptable carrier.

14. A method for suppressing the expression of a target gene, comprising a step of introducing the double-stranded lipid-modified RNA of claim 1 into a cell.

* * * * *